United States Patent
Jo et al.

(10) Patent No.: US 10,590,496 B2
(45) Date of Patent: Mar. 17, 2020

(54) COMPOSITION FOR PREVENTING AND TREATING DEGENERATIVE BRAIN DISEASE USING NOVEL LACTIC ACID BACTERIA

(71) Applicant: WEDEA INC., Daejeon (KR)

(72) Inventors: Su Yeon Jo, Daejeon (KR); Se Hyeok Min, Daejeon (KR); Seok Jin Yun, Daejeon (KR); Do Hee Kim, Anyang-si (KR)

(73) Assignee: WEDEA INC., Daejeon (KR)

( * ) Notice: Subject to any disclaimer, the term of this patent is extended or adjusted under 35 U.S.C. 154(b) by 113 days.

(21) Appl. No.: 15/701,928

(22) Filed: Sep. 12, 2017

(65) Prior Publication Data

US 2018/0148801 A1    May 31, 2018

(30) Foreign Application Priority Data

Nov. 29, 2016 (KR) .................. 10-2016-0160188
Aug. 14, 2017 (KR) .................. 10-2017-0103015

(51) Int. Cl.

| | | |
|---|---|---|
| C12R 1/225 | (2006.01) | |
| C12N 1/20 | (2006.01) | |
| A23L 33/10 | (2016.01) | |
| A23L 33/135 | (2016.01) | |
| A23L 33/00 | (2016.01) | |
| A61K 31/195 | (2006.01) | |
| A61K 35/747 | (2015.01) | |
| A23L 33/175 | (2016.01) | |
| A61K 35/00 | (2006.01) | |

(52) U.S. Cl.
CPC .............. *C12R 1/225* (2013.01); *A23L 33/10* (2016.08); *A23L 33/135* (2016.08); *A23L 33/175* (2016.08); *A23L 33/40* (2016.08); *A61K 31/195* (2013.01); *C12N 1/20* (2013.01); *A23V 2002/00* (2013.01); *A23Y 2220/71* (2013.01); *A61K 35/747* (2013.01); *A61K 2035/11* (2013.01)

(58) Field of Classification Search
CPC ...... C12R 1/225; A23L 33/40; A23Y 2220/71
See application file for complete search history.

(56) References Cited

U.S. PATENT DOCUMENTS

| | | |
|---|---|---|
| 2005/0100531 A1 | 5/2005 | Bienenstock |
| 2011/0217368 A1 | 9/2011 | Prakash et al. |
| 2013/0011337 A1 | 1/2013 | Kuroiwa et al. |

FOREIGN PATENT DOCUMENTS

| | | |
|---|---|---|
| KR | 1020040037011 A | 5/2004 |
| KR | 1020100014718 A | 2/2010 |
| KR | 1020110057550 A | 6/2011 |
| KR | 1020120015335 A | 2/2012 |
| KR | 101426275 B1 | 8/2014 |
| KR | 1020160131928 A | 11/2016 |

OTHER PUBLICATIONS

Li et al., Animal Models Exp Med. 2018, vol. 1, p. 180-188.*
"Alzheimer's Disease Fact Sheet" and "How Is Alzheimer's Disease Treated", HIH, National Institute on Aging, retrieved from nia.nih.gov/health/how-alzheimers-disease-treated, on Jul. 31, 2019, 18 pages of PDF.*
Alkasir et al., "Human gut microbiota: the links with dementia development", Protein Cell, Feb. 2017, pp. 90-102, vol. 8:2.

* cited by examiner

*Primary Examiner* — Kade Ariani
(74) *Attorney, Agent, or Firm* — The Webb Law Firm

(57) ABSTRACT

Provided is a composition containing *Lactobacillus reuteri* ELF corresponding to a novel lactic acid bacteria strain and 5-aminolevulinic acid. The composition may be significantly effective to prevent and treat degenerative brain disease and have excellent anti-obesity and anti-diabetes effects, such that the present invention may provide various pharmaceutical composition, health foods, and the like, using the same.

4 Claims, 16 Drawing Sheets

Specification includes a Sequence Listing.

FIG. 31

```
AGTCGTACGCACTGGCCCAACTGATTGATGGTGCTTGCACCTGATTGACGATGGATCACC
AGTGAGTGGCGGACGGGTGAGTAACACGTAGGTAACCTGCCCCGGAGCGGGGGATAACAT
TTGGAAACAGATGCTAATACCGCATAACAACAAAAGCCACATGGCTTTTGTTTGAAAGAT
GGCTTTGGCTATCACTCTGGGATGGACCTGCGGTGCATTAGCTAGTTGGTAAGGTAACGG
CTTACCAAGGCGATGATGCATAGCCGAGTTGAGAGACTGATCGGCCACAATGGAACTGAG
ACACGGTCCATACTCCTACGGGAGGCAGCAGTAGGGAATCTTCCACAATGGGCGCAAGCC
TGATGGAGCAACACCGCGTGAGTGAAGAAGGGTTTCGGCTCGTAAAGCTCTGTTGTTGGA
GAAGAACGTGCGTGAGAGTAACTGTTCACGCAGTGACGGTATCCAACCAGAAAGTCACGG
CTAACTACGTGCCAGCAGCCGCGGTAATACGTAGGTGGCAAGCGTTATCCGGATTTATTG
GGCGTAAAGCGAGCGCAGGCGGTTGCTTAGGTCTGATGTGAAAGCCTTCGGCTTAACCGA
AGAAGTGCATCGGAAACCGGGCGACTTGAGTGCAGAAGAGGACAGTGGAACTCCATGTGT
AGCGGTGGAATGCGTAGATATATGGAAGAACACCAGTGGCGAAGGCGGCTGTCTGGTCTG
CAACTGACGCTGAGGCTCGAAAGCATGGGTAGCGAACAGGATTAGATACCCTGGTAGTCC
ATGCCGTAAACGATGAGTGCTAGGTGTTGGAGGGTTTCCGCCCTTCAGTGCCGGAGCTAA
CGCATTAAGCACTCCGCCTGGGGAGTACGACCGCAAGGTTGAAACTCAAAGGAATTGACG
GGGGCCCGCACAAGCGGTGGAGCATGTGGTTTAATTCGAAGCTACGCGAAGAACCTTACC
AGGTCTTGACATCTTGCGCTAACCTTAGAGATAAGGCGTTCCCTTCGGGGACGCAATGAC
AGGTGGTGCATGGTCGTCGTCAGCTCGTGTCGTGAGATGTTGGGTTAAGTCCCGCAACGA
GCGCAACCCTTGTTACTAGTTGCCAGCATTAAGTTGGGCACTCTAGTGAGACTGCCGGTG
ACAAACCGGAGGAAGGTGGGGACGACGTCAGATCATCATGCCCCTTATGACCTGGGCTAC
ACACGTGCTACAATGGACGGTACAACGAGTCGCAAGCTCGCGAGAGTAAGCTAATCTCTT
AAAGCCGTTCTCAGTTCGGACTGTAGGCTGCAACTCGCCTACACGAAGTCGGAATCGCTA
GTAATCGCGGATCAGCATGCCGCGGTGAATACGTTCCCGGGCCTTGTACACACCGCCCGT
CACACCATGGGAGTTTGTAACGCCCAAAGTCGGTGGCCTAACCTTTA
```

FIG. 32

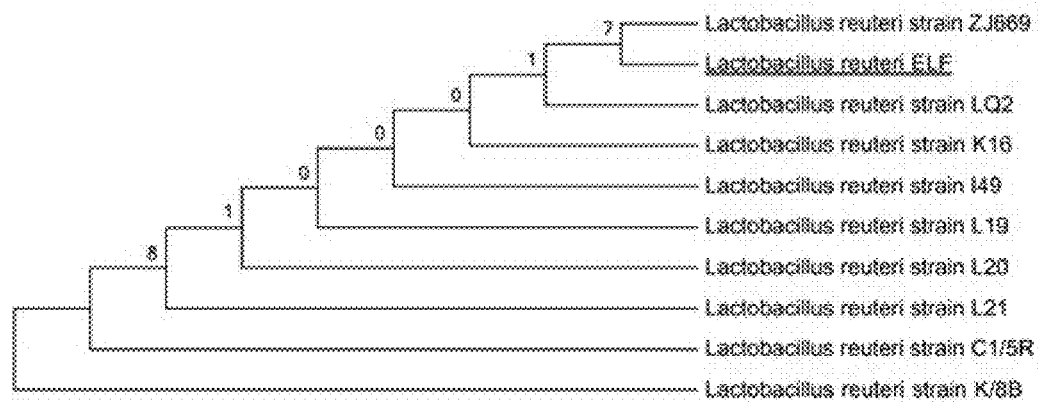

```
                            SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: forward AMPK-alpha1 primer

<400> SEQUENCE: 1
aagccgaccc aatgacatca                                                    20

<210> SEQ ID NO 2
<211> LENGTH: 20
<212> TYPE: DNA
<213> ORGANISM: Artificial Sequence
<220> FEATURE:
<223> OTHER INFORMATION: reverse AMPK-alpha1 primer

<400> SEQUENCE: 2
cttccttcgt acacgcaaat                                                    20

<210> SEQ ID NO 3
<211> LENGTH: 23
<212> TYPE: DNA
<213> ORGANISM: Artificial Sequence
<220> FEATURE:
<223> OTHER INFORMATION: sense probe

<400> SEQUENCE: 3
ttcaaatgag attgtgggaa aat                                                23

<210> SEQ ID NO 4
<211> LENGTH: 22
<212> TYPE: DNA
<213> ORGANISM: Artificial Sequence
<220> FEATURE:
<223> OTHER INFORMATION: antisense probe

<400> SEQUENCE: 4
accgatacag tacagtacag ta                                                 22

<210> SEQ ID NO 5
<211> LENGTH: 1427
<212> TYPE: DNA
<213> ORGANISM: Lactobacillus reuteri

<400> SEQUENCE: 5
agtcgtacgc actggcccaa ctgattgatg gtgcttgcac ctgattgacg atggatcacc        60
agtgagtggc ggacgggtga gtaacacgta ggtaacctgc cccggagcgg gggataacat       120
ttggaaacag atgctaatac cgcataacaa caaaagccac atggcttttg tttgaaagat       180
ggctttggct atcactctgg gatggacctg cggtgcatta gctagttggt aaggtaacgg       240
cttaccaagg cgatgatgca tagccgagtt gagagactga tcggccacaa tggaactgag       300
acacggtcca tactcctacg ggaggcagca gtagggaatc ttccacaatg ggcgcaagcc       360
tgatggagca acaccgcgtg agtgaagaag ggtttcggct cgtaaagctc tgttgttgga       420
gaagaacgtg cgtgagagta actgttcacg cagtgacggt atccaaccag aaagtcacgg       480
```

```
ctaactacgt gccagcagcc gcggtaatac gtaggtggca agcgttatcc ggatttattg    540
ggcgtaaagc gagcgcaggc ggttgcttag gtctgatgtg aaagccttcg gcttaaccga    600
agaagtgcat cggaaaccgg gcgacttgag tgcagaagag gacagtggaa ctccatgtgt    660
agcggtggaa tgcgtagata tatggaagaa caccagtggc gaaggcggct gtctggtctg    720
caactgacgc tgaggctcga aagcatgggt agcgaacagg attagatacc ctggtagtcc    780
atgccgtaaa cgatgagtgc taggtgttgg agggtttccg cccttcagtg ccggagctaa    840
cgcattaagc actccgcctg gggagtacga ccgcaaggtt gaaactcaaa ggaattgacg    900
ggggcccgca caagcggtgg agcatgtggt ttaattcgaa gctacgcgaa gaaccttacc    960
aggtcttgac atcttgcgct aaccttagag ataaggcgtt cccttcgggg acgcaatgac   1020
aggtggtgca tggtcgtcgt cagctcgtgt cgtgagatgt tgggttaagt cccgcaacga   1080
gcgcaaccct tgttactagt tgccagcatt aagttgggca ctctagtgag actgccggtg   1140
acaaaccgga ggaaggtggg gacgacgtca gatcatcatg cccttatga cctgggctac   1200 acacgtgcta caatggacgg tacaacgagt cgcaagctcg cgagagtaag ctaatctctt   1260
aaagccgttc tcagttcgga ctgtaggctg caactcgcct acacgaagtc ggaatcgcta   1320
gtaatcgcgg atcagcatgc cgcggtgaat acgttcccgg gccttgtaca caccgcccgt   1380
cacaccatgg gagtttgtaa cgcccaaagt cggtggccta acctta              1427
```

COMPOSITION FOR PREVENTING AND TREATING DEGENERATIVE BRAIN DISEASE USING NOVEL LACTIC ACID BACTERIA

CROSS-REFERENCE TO RELATED APPLICATIONS

This application claims priority to Korean Patent Application Nos. 10-2016-0160188 and 10-2017-0103015, filed Nov. 29, 2016 and Aug. 14, 2017, respectively, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1707683_ST25.txt. The size of the text file is 3,066 bytes, and the text file was created on Sep. 7, 2017.

TECHNICAL FIELD

The present invention relates to a composition for preventing and treating a degenerative disease using novel lactic acid bacteria.

BACKGROUND ART

It was known that lactic acid bacteria produce various kinds of metabolites through metabolism, and some of the metabolites perform various useful functions such as a function of inhibiting proliferation of intestinal harmful bacteria, a function of suppressing production of harmful materials, a function of alleviating inflammatory diseases, a function of alleviating cardiovascular diseases, a function of lowering a cholesterol level, and the like, such that the lactic acid bacteria have been used to prepare health food and medical formulations.

The lactic acid bacteria may decompose a specific harmful material in the body through metabolism depending on the kind of lactic acid bacteria, produce a specific material depending on a material used in the metabolism, and increase an absorption rate of a specific material in the body. For example, a food composition containing *Lactobacillus reuteri* for preventing obesity or diabetes has been disclosed in Korean Patent Laid-Open Publication No. 2004-0037011, and an anti-obesity composition containing a mixture of several kinds of lactic acid bacteria has been disclosed in Korean Patent No. 1426275.

5-aminolevulinic acid is an intermediate of a porphyrin biosynthesis process, and porphyrin, which is a metal ion composite fixed in a tetrapyrrole ring, may be used to perform an important function in the body. For example, chlorophyll, hemoglobin, and myoglobin correspond to composites containing porphyrin as a core structure and different metal ions from each other. It is known that 5-aminolevulinic acid is dehydrated by 5-aminolevulinic acid dehydratase corresponding to dehydratase, such that porphobilinogen is formed as a dimmer, and porphobilinogen is converted into protoporphyrin through uroporphyrin.

Protoporphyrin produced from 5-aminolevulinic acid may be used as an acne therapeutic agent or an ingredient used for skin cancer photodynamic therapy, such that 5-aminolevulinic acid is used to produce protoporphyrin. However, since porphobilinogen, which is an intermediate product, has an unstable property and synthesis and purification of porphobilinogen are difficult, porphobilinogen corresponds to an expensive compound. Further, since it is predicted that porphobilinogen will be continuously converted into protoporphyrin, there are few studies on porphobilinogen.

In order to study new uses of lactic acid bacteria and a pyrrole compound including porphobilinogen, the present inventors isolated and identified novel lactic acid bacteria. In addition, while treating 5-aminolevulinic acid and the novel lactic acid bacteria together, the present inventors confirmed that the novel lactic acid bacteria and metabolites thereof have an excellent effect on a degenerative brain disease, diabetes, and obesity, thereby completing the present invention.

RELATED ART DOCUMENT

Patent Document

Korean Patent Laid-Open Publication No. 2004-0037011
Korean Patent No. 1426275

DISCLOSURE

Technical Problem

An object of the present invention is to provide a composition for improving health using *Lactobacillus reuteri* ELF (accession number: KCTC 13154BP) corresponding to a novel strain.

Another object of the present invention is to provide a composition for treating a disease using *Lactobacillus reuteri* ELF corresponding to a novel strain.

Another object of the present invention is to provide a composition for improving health containing *Lactobacillus reuteri* ELF corresponding to a novel strain and 5-aminolevulinic acid.

Another object of the present invention is to provide a composition for treating a disease containing *Lactobacillus reuteri* ELF corresponding to a novel strain and 5-aminolevulinic acid.

Technical Solution

In one general aspect, a health functional food composition for preventing or treating a degenerative brain disease contains *Lactobacillus reuteri* ELF (accession number: KCTC 13154BP) corresponding to a novel strain.

In another general aspect, a pharmaceutical composition for preventing or treating a degenerative brain disease contains *Lactobacillus reuteri* ELF (accession number: KCTC 13154BP) corresponding to a novel strain.

In another general aspect, a health functional food composition for preventing or treating obesity contains *Lactobacillus reuteri* ELF (accession number: KCTC 13154BP) corresponding to a novel strain.

In another general aspect, a pharmaceutical composition for preventing or treating obesity contains *Lactobacillus reuteri* ELF (accession number: KCTC 13154BP) corresponding to a novel strain.

In another general aspect, a health functional food composition for preventing or treating diabetes contains *Lactobacillus reuteri* ELF (accession number: KCTC 13154BP) corresponding to a novel strain.

In another general aspect, a pharmaceutical composition for preventing or treating diabetes contains *Lactobacillus reuteri* ELF (accession number: KCTC 13154BP) corresponding to a novel strain.

In another general aspect, a health functional food composition for preventing or treating a degenerative brain disease contains: *Lactobacillus reuteri* ELF (accession number: KCTC 13154BP) corresponding to a novel strain, and 5-aminolevulinic acid.

In another general aspect, a pharmaceutical composition for preventing or treating a degenerative brain disease contains: *Lactobacillus reuteri* ELF (accession number: KCTC 13154BP) corresponding to a novel strain; and 5-aminolevulinic acid.

In another general aspect, a health functional food composition for preventing or treating obesity contains: *Lactobacillus reuteri* ELF (accession number: KCTC 13154BP) corresponding to a novel strain; and 5-aminolevulinic acid.

In another general aspect, a pharmaceutical composition for preventing or treating obesity contains: *Lactobacillus reuteri* ELF (accession number: KCTC 13154BP) corresponding to a novel strain; and 5-aminolevulinic acid.

In another general aspect, a health functional food composition for preventing or treating diabetes contains: *Lactobacillus reuteri* ELF (accession number: KCTC 13154BP) corresponding to a novel strain; and 5-aminolevulinic acid.

In another general aspect, a pharmaceutical composition for preventing or treating diabetes contains: *Lactobacillus reuteri* ELF (accession number: KCTC 13154BP) corresponding to a novel strain; and 5-aminolevulinic acid.

Advantageous Effects

A composition containing *Lactobacillus reuteri* ELF (accession number: KCTC 13154BP) corresponding to a novel strain according to the present invention may be easily ingested and there is no adverse effect.

The composition containing *Lactobacillus reuteri* ELF (accession number: KCTC 13154BP) corresponding to the novel strain according to the present invention may be significantly effective to prevent and treat a degenerative brain disease. Particularly, the composition may be significantly effective to prevent and treat Alzheimer's disease among degenerative brain diseases.

The composition containing *Lactobacillus reuteri* ELF corresponding to the novel strain according to the present invention may be significantly effective to prevent and treat diabetes.

The composition containing *Lactobacillus reuteri* ELF corresponding to the novel strain according to the present invention may be significantly effective to prevent and treat obesity.

The *Lactobacillus reuteri* ELF corresponding to the novel strain according to the present invention may produce a pyrrole based compound with significantly high efficiency as compared to *Lactobacillus reuteri* known in the art.

The *Lactobacillus reuteri* ELF corresponding to the novel strain according to the present invention may produce various pyrrole based compounds such as porphobilinogen, hydroxymethylbilane, porphyrinogen, preuroporphyrinogen, uroporphyrinogen, hepta-carboxylate porphyrinogen, hexa-carboxylate porphyrinogen, penta-carboxylate porphyrinogen, coproporphyrinogen, protoporphyrin, protoporphyrinogen, heme, chlorophyll, which are metabolites of 5-aminolevulinic acid, and derivatives thereof from 5-aminolevulinic acid with high efficiency. Particularly, the *Lactobacillus reuteri* ELF may produce porphobilinogen from 5-aminolevulinic acid with high efficiency, such that the *Lactobacillus reuteri* ELF may be significantly effectively used to prevent and treat a degenerative brain disease, diabetes, and obesity.

DESCRIPTION OF DRAWINGS

FIG. 31 shows a 16S rRNA gene sequence (SEQ ID NO: 5) of *Lactobacillus reuteri* ELF (accession number: KCTC 13154BP).

FIG. 32 shows a phylogenetic tree of *Lactobacillus reuteri* ELF (accession number: KCTC 13154BP).

DESCRIPTION OF THE INVENTION

Figure 1:
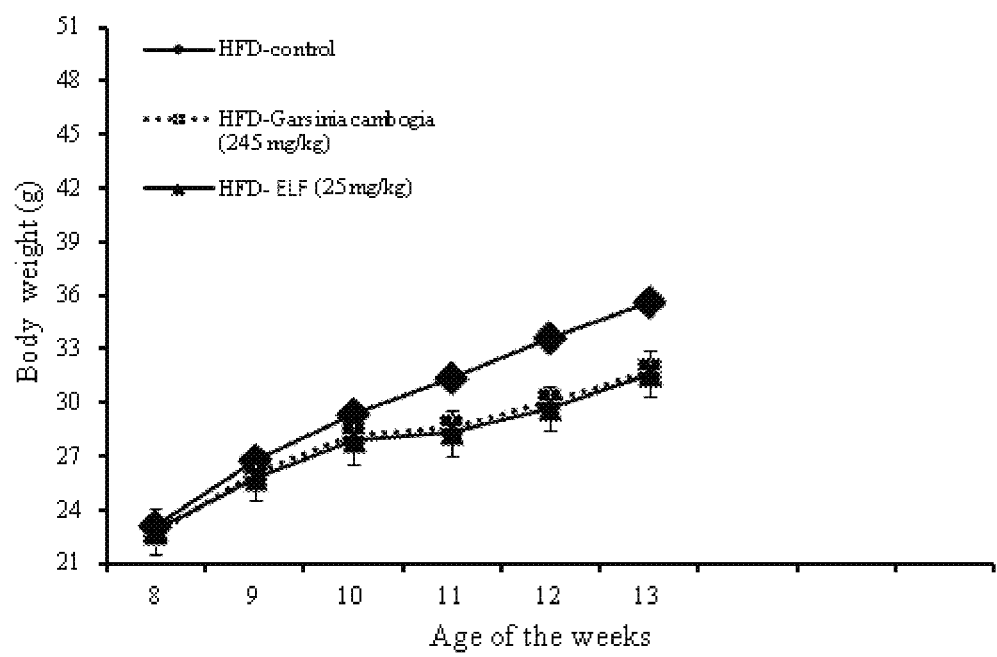
FIG. 1 illustrates changes in body weight by *Lactobacillus reuteri* ELF (accession number: KCTC 13154BP).

Hereinafter, the present invention will be described in more detail. A description for the known functions and configurations obscuring the gist of the present invention will be omitted in the following description and the accompanying drawings, some components illustrated in the drawings may be exaggerated or omitted in order to help the understanding of the present invention, and terms used in the present specification have the general meaning understood by those skilled in the art to which the present invention pertains unless otherwise defined.

The present invention relates to *Lactobacillus reuteri* ELF (accession number: KCTC 13154BP) corresponding to a novel strain, and a composition containing the same.

The present invention relates to a composition containing *Lactobacillus reuteri* ELF (accession number: KCTC 13154BP) corresponding to a novel strain, and 5-aminolevulinic acid.

The present inventors isolated only lactic acid bacteria from the milk of a woman using a selective medium for lactic acid bacteria, selected a strain having excellent acid resistance, bile resistance, and antibiotic resistance, and then performed a molecular phylogenetic analysis based on a 16S rRNA sequence on the selective strain, thereby isolating and identifying a *Lactobacillus reuteri* strain. In addition, the present inventors designated the isolated and identified lactic acid bacterial strain as *Lactobacillus reuteri* ELF and deposited the strain at Korean Collection for Type Cultures (KCTC) of Korea Research Institute of Bioscience and Biotechnology, 181, Ipsin-gil, Jeongeup-si, Jeolllabuk-do 56212 Republic of Korea, under an accession number KCTC 13154BP on Nov. 22, 2016.

The present invention provides a health functional food composition for preventing or treating a disease containing *Lactobacillus reuteri* ELF (accession number: KCTC 13154BP).

The present invention provides a pharmaceutical composition for preventing or treating a disease containing *Lactobacillus reuteri* ELF (accession number: KCTC 13154BP).

The present invention provides a health functional food composition for preventing or treating a disease containing *Lactobacillus reuteri* ELF (accession number: KCTC 13154BP) and 5-aminolevulinic acid (hereinafter, '5-ALA' may also be used in the same meaning as 5-aminolevulinic acid).

The present invention provides a pharmaceutical composition for preventing or treating a disease containing *Lactobacillus reuteri* ELF (accession number: KCTC 13154BP) and 5-aminolevulinic acid (hereinafter, '5-ALA' may also be used in the same meaning as 5-aminolevulinic acid).

As used herein, the term "treatment" means all actions of advantageously changing a state of a subject having a disease, for example, actions for alleviating or reducing symptoms of the disease, and the like by using the composition according to the present invention.

As used herein, the term "prevention" means all actions of suppressing or delaying occurrence of the disease using the composition according to the present invention.

In the present invention, the disease may be one or more selected from a degenerative brain disease, obesity, and diabetes.

In the present invention, the degenerative brain disease is one or more selected from Alzheimer's disease, dementia, Parkinson's disease, Huntington's chorea, Creutzfeldt-Jakob disease, type 3-diabetes corresponding to Alzheimer's disease caused by insulin resistance occurring in the brain, and Pick's disease.

*Lactobacillus reuteri* ELF (accession number: KCTC 13154BP), which is a strain isolated and identified from the milk of a woman, is a strain harmless to the body. *Lactobacillus reuteri* ELF has excellent biosafety and does not have cytotoxicity, and there is no risk of adverse effects caused by ingestion of the strain.

It is preferable that the composition according to the present invention contains a *Lactobacillus reuteri* ELF strain itself, but the present invention is not limited thereto. For example, the present invention may provide a composition containing one or more selected from dead *Lactobacillus reuteri* ELF, dried *Lactobacillus reuteri* ELF, *Lactobacillus reuteri* ELF broth, *Lactobacillus reuteri* ELF homogenates, *Lactobacillus reuteri* ELF extracts, *Lactobacillus reuteri* ELF concentrates, a culture medium of *Lactobacillus reuteri* ELF, a culture suspension containing *Lactobacillus reuteri* ELF, a filtrate of the *Lactobacillus reuteri* ELF broth, and a filtrate from which the strain is removed after centrifugation of the *Lactobacillus reuteri* ELF broth.

Particularly, the composition according to the present invention is effective to treat and prevent degenerative brain diseases including Alzheimer's disease.

According to an exemplary embodiment of the present invention, since the composition containing *Lactobacillus reuteri* ELF may reduce beta amyloid, (Aβ) and postsynaptic density protein (PSD), the composition may be effective to treat and prevent Alzheimer's disease. In addition, the composition containing *Lactobacillus reuteri* ELF may significantly inhibit beta amyloid plaque formation. Further, the composition containing *Lactobacillus reuteri* ELF does not have a direct influence on phosphorylation of tau protein or reduction of phosphorylated tau protein, but may reduce tau protein, such that the composition may be effective to treat and prevent Alzheimer's disease. That is, the composition according to the present invention may reduce both beta amyloid and tau protein, which are main factors causing Alzheimer's diseases, such that the composition may be significantly effective to treat and prevent Alzheimer's disease.

According to another exemplary embodiment of the present invention, the composition containing *Lactobacillus reuteri* ELF may inhibit an increase in glial fibrillary acidic protein (GFAP) expression, which is increased in patients with Alzheimer's disease. This effect also shows that the composition containing *Lactobacillus reuteri* ELF according to the present invention is effective to treat and prevent Alzheimer's disease.

*Lactobacillus reuteri* ELF (accession number: KCTC 13154BP) itself, which the novel strain according to the present invention, has significantly high productivity in view of production of a pyrrole based compound. Further, *Lactobacillus reuteri* ELF may metabolize a precursor compound capable of producing the pyrrole based compound such as 5-aminolevulinic acid to produce a specific pyrrole based compound with high efficiency. Particularly, *Lactobacillus reuteri* ELF may significantly increase a content of porphobilinogen (hereinafter, 'PBG' may also be used in the same meaning as porphobilinogen) among the pyrrole based compounds. Since porphobilinogen may improve functional aspect of lactic acid bacteria, the composition containing *Lactobacillus reuteri* ELF may more effectively treat and prevent diseases as compared to compositions containing other lactic acid bacteria. According to the exemplary embodiment of the present invention, an amount of the pyrrole based compound produced by *Lactobacillus reuteri* ELF may be at least six times larger than that of a pyrrole based compound produced by *Lactobacillus reuteri* known in the art.

In the present invention, it is known that 5-aminolevulinic acid is biosynthesized from glycine and succinyl-CoA by 5-aminolevulinic acid synthase, and 5-aminolevulinic acid may be represented by Chemical Formula $C_5H_9NO_3$. Further, a 5-aminolevulinic acid derivative may also be used. 5-aminolevulinic acid may be converted into porphobilinogen by porphobilinogen synthase and various materials may be converted from porphobilinogen. For example, porphobilinogen may be converted into protoporphyrin IX through an uroporphyrinogen intermediate, and further converted into heme or chlorophyll.

According to the present invention, 5-aminolevulinic acid and various biosynthetic compounds converted from 5-aminolevulinic acid may be obtained with high efficiency through metabolism of *Lactobacillus reuteri* ELF corresponding to the novel lactic acid bacteria. In addition, *Lactobacillus reuteri* ELF and metabolites thereof do not have toxicity or adverse effects, such that there is no need to separately separate *Lactobacillus reuteri* ELF or a specific metabolite thereof. That is, it is possible to obtain an effect of preventing and treating degenerative brain disease without other adverse effects by directly ingesting a composition containing *Lactobacillus reuteri* ELF and metabolites thereof as they are. Further, it is possible to obtain anti-obesity and anti-diabetic effects without other adverse effects by directly ingesting the composition containing *Lactobacillus reuteri* ELF and metabolites thereof as they are.

According to the present invention, *Lactobacillus reuteri* ELF corresponding to the novel lactic acid bacteria may metabolize 5-aminolevulinic acid to produce various compounds capable of being converted from 5-aminolevulinic acid as metabolites. It was shown that a composition containing the metabolites produced from *Lactobacillus reuteri* ELF and 5-aminolevulinic acid was particularly effective to treat degenerative brain disease and had excellent anti-obesity and anti-diabetes effect and immune enhancing effect.

Since the composition according to the present invention increase cytochrome c oxidase (COX) activity in the brain mitochondria, the composition may be significantly effective to treat the degenerative brain diseases including Alzheimer's disease.

Generally, since a blood-brain barrier (BBB) is present in the brain, in most cases, a pharmaceutical composition does not reach the brain, such that the pharmaceutical composition does not act on the brain. However, according to the exemplary embodiment of the present invention, at the time of administering the composition according to the present invention, the COX activity may be rapidly increased in the mitochondria of brain cells, such that the composition according to the present invention may directly act on the brain. The COX activity is directly associated particularly with Alzheimer's diseases among the degenerative brain diseases. That is, in patients with Alzheimer's diseases, the COX activity is low as compared to normal persons. Particularly, in the hippocampus, the COX activity is decreased by 30% or more, and thus, free radicals are increased to cause direct disorders in the brain, thereby causing Alzheimer's disease. In addition, in the blood platelet of the patient with Alzheimer's disease, COX activity is decreased, and active oxygen is increased. Further, it was already widely known that suppression of COX generated by an inflammatory response helps to enhance cognitive functions. Further, it was already confirmed that COX inhibitors are effective against psychotic disorders.

That is, the composition according to the present invention may directly increase the COX activity in the brain mitochondria, such that the composition may be significantly effective to treat and prevent the degenerative diseases including Alzheimer's disease.

According to the exemplary embodiment of the present invention, the composition containing *Lactobacillus reuteri* ELF may enhance long-term memory, such that the composition may be effective to treat and prevent the degenerative diseases including Alzheimer's disease. Further, the composition may be effective to treat cognitive impairment such as memory deficit, aphasia, agnosia, memory impairment, and the like. Cognitive impairment may include cognitive deficit caused by the degenerative brain diseases such as Alzheimer's disease, Alzheimer's dementia, senile dementia, and Parkinson's disease, cognitive deficit caused by the aging, cognitive deficit by trauma or mental shock, autism, attention deficit, and the like, but is not limited thereto.

Further, since overweight or obesity increases a level of neurofibrillary tangles or forms proteins forming brain plaques, such that overweight or obesity may become a main cause of Alzheimer's disease, such that a composition having an anti-obesity effect may be more effective to treat or prevent Alzheimer's disease.

Further, obesity is highly likely to accompany diabetes, and among diabetes, type 3 diabetes caused by insulin resistance in the brain is significantly highly associated with occurrence of Alzheimer's disease. That is, epidemiologically, insulin deficiency and insulin resistance in the brain as well as mitochondrial dysfunction, oxidative stress, DNA damage, beta amyloid deposition, which are main causes of Alzheimer's disease, may also cause the degenerative brain diseases such as Alzheimer's disease. Therefore, treatment of Type 3 diabetes due to insulin resistance in the brain may treat and prevent the degenerative diseases including Alzheimer's disease.

According to the exemplary embodiment of the present invention, the composition according to the present invention may decrease a body weight and a blood glucose concentration and significantly increase expression of AMPK-$\alpha$1, UCP-2, and adiponectin gene which are highly associated with obesity and diabetes. This effect means that the composition according to the present invention may have excellent anti-obesity and anti-diabetes effects and may also be effective to treat and prevent the degenerative brain diseases including Alzheimer's disease. According to another exemplary embodiment of the present invention, the composition according to the present invention may significantly increase the COX activity in the brain mitochondria, such that the composition according to the present invention may be significantly effective to prevent and treat type 3 diabetes and the degenerative brain diseases including Alzheimer's disease caused by type 3 diabetes.

Further, continuous formation and deposition of beta amyloid aggregates, which is a main cause of Alzheimer's disease, causes chronic immune activation in an immune system and anti-inflammatory dysfunctions. In addition, in a case in which three main immune cells composed of T cells, B cells, and natural killer (NK) cells are deficient, accumulation of beta amyloid is significantly increased, etc., such that immune enhancement is directly associated with treatment or prevention of Alzheimer's disease.

According to the exemplary embodiment of the present invention, the composition according to the present invention may increase proliferation and activities of T lymphocytes, B lymphocytes, and NK cells. Further, production of various cytokines may be increased by the T lymphocytes, the B lymphocytes, and the NK cells. In addition, the composition according to the present invention may also increase an activity of macrophages. As a specific example, the composition according to the present invention may increase proliferation and activities of CD3 T cells, Th lymphocytes, $CD4^+$ $CD25^+$ cells, Gr-1/CD11b cells, NK cells, and macrophages. In addition, the composition according to the present invention may increase lymphocytes in the abdominal cavity. Further, the composition according to the present invention may increase production amounts of natural killer group 2 member D (NKG2D), interleukin (IL)-2, IL-4, and interferon (IFN)-$\gamma$ by cells associated with immunity. This effect means that the composition according to the present invention may be effective in enhancing immunity and may also be effective to treat and prevent the degenerative brain diseases including Alzheimer's disease. In consideration of relationship between an increase in COX activity in the brain mitochondria, the anti-diabetes effect, the anti-obesity effect, and the immune enhancing effect as described above, and treatment and prevention of Alzheimer's disease, the composition according to the present invention may be significantly effective to treat Alzheimer's disease.

According to the present invention, in *Lactobacillus reuteri* ELF corresponding to a novel *lactobacillus* strain, a content of pyrrole compound is higher than that in other *Lactobacillus reuteri* species. Further, a property of *Lactobacillus reuteri* ELF to produce pyrrole compounds including porphobilinogen from 5-aminolevulinic acid is significantly excellent as compared to other *Lactobacillus reuteri* species.

In the present invention, the metabolites produced from 5-aminolevulinic acid by metabolism of lactic acid bacteria include 5-aminolevulinic acid, porphobilinogen, hydroxymethylbilane, porphyrinogen derivatives, and porphyrin derivatives. For example, the metabolites may include one or more selected from 5-aminolevulinic acid, porphobilinogen, hydroxymethylbilane, porphyrinogen, preuroporphyrinogen, uroporphyrinogen, hepta-carboxylate porphyrinogen, hexa-carboxylate porphyrinogen, penta-carboxylate porphyrinogen, coproporphyrinogen, protoporphyrin, protoporphyrinogen, heme, and chlorophyll. In addition, the metabolites include uroporphyrinogens and coproporphyrinogens I to IV depending on the form thereof, and include protoporphyrin IX which is mainly present in the nature as the protoporphyrin. Further, the composition according to the present invention may contain derivatives of each of the metabolites or salts thereof.

According to the exemplary embodiment of the present invention, in the case in which both *Lactobacillus reuteri* ELF and the metabolites of 5-aminolevulinic acid produced by metabolism of *Lactobacillus reuteri* ELF are contained, the effects associated with treatment of the degenerative brain disease and immune enhancement, and anti-obesity and anti-diabetes effects may be excellent as compared to the case in which metabolism of only *Lactobacillus reuteri* ELF is carried out under the same conditions without adding 5-aminolevulinc acid and the case in which only 5-aminolevulinic acid is added.

In the composition containing *Lactobacillus reuteri* ELF according to the present invention and the metabolites produced from 5-aminolevulinic acid by metabolism of *Lactobacillus reuteri* ELF, mechanism of each of the ingredients contained in the metabolites acting on treatment of the degenerative brain disease and immune enhancement, and anti-obesity and anti-diabetes effects is not clear. However, it is assumed that some or all of the metabolites produced from 5-aminolevulinic acid by *Lactobacillus reuteri* ELF act together with *Lactobacillus reuteri* ELF, thereby creating a synergistic effect. For example, as one of the metabolites, porphobilinogen known to be unstable may be stably produced with high efficiency by *Lactobacillus reuteri* ELF, and it is assumed that this feature is one of factors having an important influence on the effects of the composition according to the present invention.

A formulation of the health functional food composition according to the present invention is not limited. For example, the health functional food composition may be formulated into a solid, a liquid, or the like. It is preferable that the health functional food composition may be formulated into a drink, a pill, a tablet, a powder, a capsule, or the like. Further, a functional food may be prepared by adding various types of food additives thereto. Specific examples of the functional food may include meat, sausage, bread, chocolates, candies, snacks, confectionery, pizza, ramen, other noodles, gums, dairy products including ice cream, various soups, beverages, tea, drinks, alcoholic beverages, vitamin complexes, and the like.

The pharmaceutical composition according to the present invention may be prepared by culturing the lactic acid bacteria itself or adding 5-aminolevulinic acid to the lactic acid bacteria and culturing the lactic acid bacterial according to a general method of culturing lactic acid bacteria. Culturing conditions may be adjusted for preferable culturing depending on the kind of used lactic acid bacteria. As an example of a preparation method according to the exemplary embodiment of the present invention, a preparation method including: preparing distilled water from which dissolved oxygen is removed by bubbling inert gas; adding 5-aminolevulinic acid to the prepared distilled water, adjusting a pH to 8.5 to 9.5; adding lactic acid bacteria thereto; stirring the mixture at 25 to 40° C. for 10 to 24 hours; and then obtaining the lactic acid bacteria and metabolites produced by metabolism of the lactic acid bacteria by centrifugation may be used. Here, the preparation method may further include, after the obtaining of the lactic acid bacteria and metabolites produced by the lactic acid bacteria, freeze-drying the obtained lactic acid bacteria and metabolites.

According to the present invention, in the obtaining of the lactic acid bacteria and metabolites produced by the lactic acid bacteria, the lactic acid bacteria and the metabolites thereof precipitated by centrifugation after stirring may be obtained, and the obtained lactic acid bacteria and metabolites may be used as they are without separately removing the lactic acid bacteria or isolating or purifying only the metabolites.

The composition may be prepared by obtaining the lactic acid bacteria and the metabolites thereof and removing a predetermined amount of water, but the composition capable of having more excellent effects and being more easily processed may be prepared by a freeze-drying process, and be formulated in various formulations.

The composition according to the present invention may contain a pharmaceutically acceptable carrier. The carrier capable of being contained in the composition according to the present invention may be starch, acacia rubber, water, syrup, cellulose, gelatin, minerals, oil, talc, polysaccharides, or the like, which is generally used in preparations, but is not limited thereto. A sweetener, a flavoring agent, a preservative, a wetting agent, or the like, in addition to the carrier may be additionally contained.

The pharmaceutical composition according to the present invention may be formulated by those skilled in the art using the pharmaceutically acceptable carrier or excipient, or a mixture thereof. A formulation of the composition according to the present invention is not limited. An example of the formulation of the composition may include solutions, emulsions, powders, granules, tablets, and capsules, and a stabilizer or dispersant may be additionally contained.

The composition according to the present invention may be immediately ingested, such that the composition may be prepared as functional health food or contained in general food.

Hereinafter, Examples of the present invention will be described in detail, but the following Examples are provided as preferable examples of the present invention. Therefore, the present invention is not limited thereto.

Example 1

Isolation and Identification of *Lactobacillus reuteri* ELF

A facultative anaerobic bacteria strain isolated from milk of a healthy woman was spread on a MRS medium containing 1.5% agar and cultured at 37° C. for 24 hours, and it was confirmed that the strain was purely isolated. For identification and classification of a lactic acid bacteria strain, a 16S rRNA gene sequence (SEQ ID No. 1) was analyzed. This strain had an rRNA homology of 99% or more with a *Lactobacillus reuteri* standard strain, such that this strain was identified as a *Lactobacillus reuteri* strain. A *Lactobacillus reuteri* strain having the same 16S rRNA gene sequence was not detected.

Homology between a 16S rRNA sequence of an isolated *Lactobacillus reuteri* ELF strain and a gene sequence of the *Lactobacillus reuteri* standard strain in genetic information database in National Center for Biotechnology Information (NCBI) was analyzed. A phylogenetic tree was drawn using a neighbor-joining method based on Jukes-Cantor model as an analysis method (FIG. 32).

Mycological characteristics of the isolated *Lactobacillus reuteri* ELF strain and *Lactobacillus reuteri* ATCC23272 were compared and illustrated in [Table 1].

TABLE 1

| Mycological Characteristics | *Lactobacillus reuteri* ELF | *Lactobacillus reuteri* ATCC23272 |
|---|---|---|
| Production of Pyrrole Compound | ≥1.7 | 1.0 |
| Production of Reuterin | ≤0.8 | 1.0 |
| Motility | No | No |
| Shape | Bacillus | Bacillus |
| Gram Staining | Positive | Positive |
| Production of Catalase | Negative | Negative |
| Production of Oxidase | Negative | Negative |
| D-glucose metabolism | Possible | Possible |
| D-mannose metabolism | Possible | Possible |
| D-fructose metabolism | Possible | Possible |
| Lactose metabolism | Possible | Possible |
| Inositol metabolism | Possible | Possible |
| Sucrose metabolism | Possible | Possible |

* Production amounts of porphobilinogen and reuterin were measured after culturing *Lactobacillus reuteri* ELF and *Lactobacillus reuteri* ATCC23272 in the same medium for 24 hours. The production amounts were relatively compared with each other by considering the production amount by *Lactobacillus reuteri* ATCC23272 as 1.0.

The present inventors designated this strain as *Lactobacillus reuteri* ELF and deposited this strain at Korean Collection for Type Cultures (KCTC) of Korea Research Institute of Bioscience and Biotechnology under an accession number KCTC 13154BP on Nov. 22, 2016.

Example 2

Culturing of *Lactobacillus reuteri* ELF and Isolation of Pyrrole Compound

A medium based on a MRS medium and composed as in the following Table 2 was prepared.

TABLE 2

| Composition of Medium | |
|---|---|
| Ingredient | Content (g) |
| Soy Peptone PR | 10 |
| Beef extract | 10 |
| Yeast extract | 5 |
| Lactose | 20 |
| Tween 80 | 1 |
| Citric acid | 2 |
| Sodium acetate | 5 |
| Magnesium sulfate | 0.1 |
| Manganese sulfate food additive | 0.05 |
| Dipotassium phosphate | 2 |
| Glutamic acid | 1 |
| 10% L-Carnitine base | 5 |
| Water | 1 L |

After the medium was sterilized, *Lactobacillus reuteri* ELF ($1.5*10^8$ CFU/ml) was inoculated at 1% (v/v) thereinto, and cultured for 15 to 20 hours. A pH was adjusted to 6.5, and a temperature was maintained at 38° C. When the culturing was terminated, 20 μl of culture solution was extracted and added to 2 ml of Ehrlich reagent, and strong red absorbance at a wavelength of 550 nm was confirmed by UV spectroscopy ((Absorbance) λ550=0.22). The strain was isolated by centrifugation, and a filtrate was purified by the following method, thereby obtaining a pyrrole compound. 200 ml of anion exchange resin (Trilite, SAR20MB, Samyang Corp.) was prepared in a column, and 25% sodium acetate aqueous solution was allowed to sufficiently run down into the column, thereby saturating anions with acetic acid. Here, this process was continued until a white precipitation was not formed at the time of dropping a silver nitrate aqueous solution to an eluate. The column was washed with distilled water, and a pH of the eluate was adjusted to be 7.5 or less. Then, the prepared filtrate was injected into the column. Thereafter, the column was washed with a sufficient amount of distilled water, and elution was performed again using 1N acetic acid. An eluted 1N acetic acid solution was freeze-dried, thereby obtaining 370 mg of purified pyrrole compound.

Example 3

Culturing of *Lactobacillus reuteri* Known in the Art Except for *Lactobacillus reuteri* ELF and Isolation of Pyrrole Compound A pyrrole compound was isolated from *Lactobacillus reuteri* known in the art by the same method as in Example 2. As the *Lactobacillus reuteri* strain, *Lactobacillus reuteri* ATCC23272 corresponding to a strain known in the art was obtained and used.

At the time of performing an Ehrlich reagent test as in Example 2, absorbance was 0.06 (λ550=0.06). Therefore, it may be appreciated that a production amount of the pyrrole compound by *Lactobacillus reuteri* ELF was about 3 times larger than that of the pyrrole compound by *Lactobacillus reuteri* ATCC23272. However, actually, a product finally obtained using *Lactobacillus reuteri* ATCC23272 was only 50 mg through anion exchange resin purification, which was smaller than 1/7 of an amount of pyrrole compound obtained using *Lactobacillus reuteri* ELF.

Example 4

Confirmation of Effect of *Lactobacillus reuteri* ELF Reducing Body Weight

In an obesity control group (high-fat diet, HFD), after adapting 8-week old male C57BL/6J mice (Daehan Biolink Corp.) for 2 weeks under a specific pathogen-free (SPF) environment at a constant temperature (25±2° C.) and a constant humidity (50±5%) with a light period of 12 hours (light on 07:00 to 19:00) while freely supplying basic feed (AIN-76A diet) and water, high-fat diet (# D12492 60 kcal fat, Research Diets Inc, USA) was administered from 10 weeks of age (at this time, the mice had a body weight of about 24 g or more), thereby preparing an obesity mouse model.

12 g of *Lactobacillus reuteri* ELF isolated by centrifugation after culturing in Example 2 and 300 mg of the metabolite, pyrrole were well mixed with 12 kg of high-fat feed (fat content: 60%, DooYeol Biotech Corp., Korea) for a mouse. These mice were divided into two groups, and while one group was fed with the high-fat feed mixed with *Lactobacillus reuteri* ELF and the metabolite thereof, and the other group was fed with a normal high-fat feed, changes in body weight were continuously observed. In a positive control group, 245 mg/kg of Garcinia cambogia extracts were used. In the mice fed with the feed mixed with *Lactobacillus reuteri* ELF, a similar effect as that in the case of using Garcinia cambogia extracts was exhibited (FIG. 1).

Example 5

Contexture Fear Conditioning Test

As a first group, 10 Alzheimer's disease-induced mice 5XFAD (Tg6799:B6SJL genetic background, 16 weeks old) were prepared, and as a second group (control group), 10 normal mice were prepared. 5 mice in each of the first and second groups were fed with normal feed mixed with *Lactobacillus reuteri* ELF obtained by centrifugation after culturing in Example 2, and the other 5 mice in each of the first and second groups were fed with normal feed that was not mixed with *Lactobacillus reuteri* ELF. After all of the mice were feely fed with feed and freely acted for 5 to 7 days, an experiment was performed. 12 g of *Lactobacillus reuteri* ELF was uniformly mixed with 12 kg of normal feed (DooYeol Biotech Corp., Seoul) and prepared in a pellet form to thereby be supplied to the mice as feed. Amounts of feed ingested by all mice were equal to each other.

A contexture fear conditioning test was performed while test conditions known in the art were suitably changed as described below. Test was performed using four standard conditioning chambers. Each of the chambers was composed of soundproof separation partitions and had a stainless steel grid bottom connected to a solid-state shock scrambler. Each of the scramblers was connected to an electronic constant current shock source controlled by an interface connected to a window computer performing a FreezeFrame software (Coulbourn Instruments, Allentown, Pa.). A digital camera was installed at a ceiling of each of the chambers, and actions of the mice were analyzed. At the time of mouse training, the mice were released so as to freely get around for 3 minutes for adaptation to a chamber context, and a footshock (1.0 Ma, 2 seconds) was applied to the conditioning chamber three to five times at an interval of 1 minute. After applying a final footshock, the mice were kept in the chamber for 30 seconds. Hippocampus-dependent contextual fear memory formation and remote memory stabilization were evaluated through freezing behaviors, immobility for 3 minutes except for respiration, when each of the mice was placed back into the same conditioning chamber after 1 and 30 days of the training. An automated FreezeFrame system digitized video signals at 4 Hz, compared movement frame by frame, recorded amounts of freezing behavior, and calculated in terms of freezing times (%).

Figure 2:
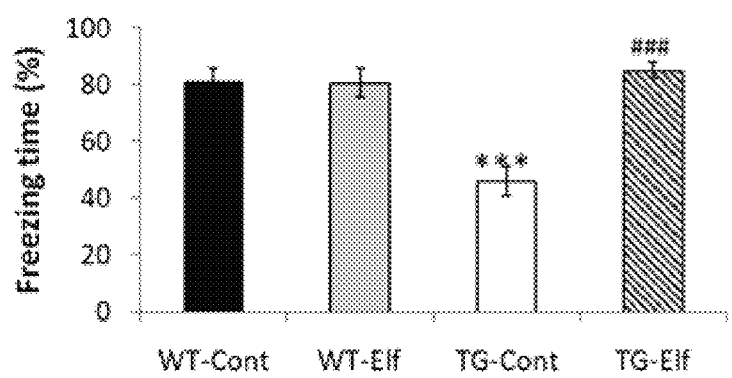
FIG. 2 illustrates changes in freezing time by *Lactobacillus reuteri* ELF (accession number: KCTC 13154BP) in a contexture fear conditioning test (WT-cont; normal mice fed with normal feed, WT-Elf; normal mice fed with *Lactobacillus reuteri* ELF, TG-Cont; Alzheimer's disease-induced mice fed with normal fed, and TG-Elf; Alzheimer's disease-induced mice fed with *Lactobacillus reuteri* ELF).
Figure 3:
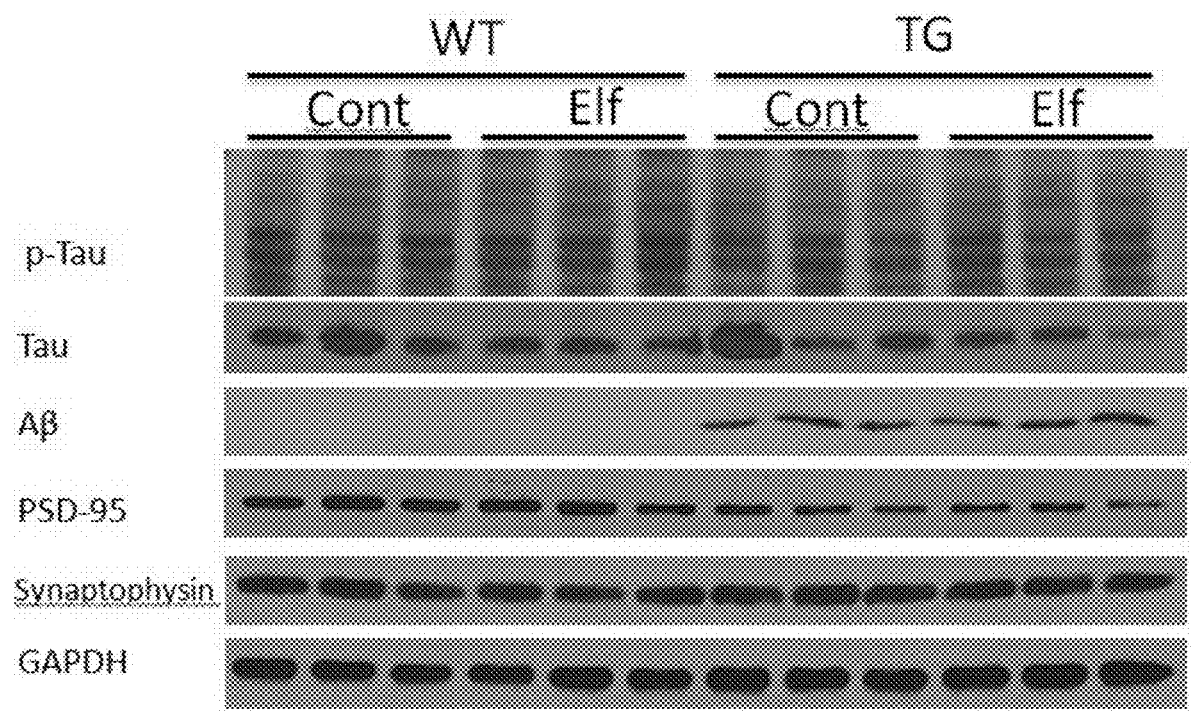
FIG. 3 illustrates western blot results of phosphorylated tau protein (p-Tau), tau protein (Tau), beta-amyloid (Aβ), postsynaptic density protein-95 (PSD-95), synaptophysin, and glyceraldehydes-3-phosphate dehydrogenase (GAPDH), which is a housekeeping gene, in normal mice (WT) and Alzheimer's disease-induced mice (TG).

As a result of the test, in genetically modified mice in which Alzheimer's disease was induced, the freezing time was significantly low, but in the genetically modified mice fed with the feed mixed with *Lactobacillus reuteri* ELF, the freezing time was recovered to a normal level (FIG. 2).

Example 6

Confirmation of Effect of *Lactobacillus reuteri* ELF Using Genetically Modified Mouse with Alzheimer's Disease As a first group, 10 Alzheimer's disease-induced mice 5XFAD (Tg6799:B6SJL genetic background, 16 weeks old) were prepared, and as a second group (control group), 10 normal mice were prepared. 5 mice in each of the first and second groups were fed with feed mixed with *Lactobacillus reuteri* ELF obtained by centrifugation after culturing in Example 2, and the other 5 mice in each of the first and second groups were normal fed with normal feed that was not mixed with *Lactobacillus reuteri* ELF. 12 g of *Lactobacillus reuteri* ELF was uniformly mixed with 12 kg of normal feed (DooYeol Biotech Corp., Seoul) and prepared in a pellet form to thereby be supplied to the mice as feed. Amounts of feed ingested by all mice were equal to each other.

After the mice in each of the groups were reared by feeding the feed for about 1 month and then sacrificed, the brain was harvested so as to include the temporal cortex, the midbrain, the cerebrum, the cerebellum, and the hippocampus, and expression of phosphorylated tau (p-Tau), Tau, amyloid beta (A β), postsynaptic density protein-95 (PSD-95), synaptophysin, and glial fibrillary acidic protein (GFAP) was measured. The presence or absence of expression was confirmed using glyceraldehyde 3-phosphate dehydrogenase (GAPDH) as a control group.

Protein expression and gene expression were confirmed by suitably changing a method known in the art. The method will be briefly described below.

After the harvested brain tissue was washed and homogenized together with a buffer, a concentration of the protein was quantified, and the proteins were separated on a gel, and transferred to a nitrocellulose membrane. After transferring, western blotting was performed using an antibody of each of the proteins.

The harvested brain tissue including the hippocampus section was immobilized on paraformaldehyde, frozen at a low temperature, and then sliced with a microtome. Thereafter, a cross section of the brain was treated with antibodies to amyloid beta and glial fibrillary acidic protein (GFAP), and observed using immunofluorescence microscope, thereby performing an immuno-staining method. At the time of staining glial fibrillary acidic protein (GFAP), as a primary antibody, a mouse monoclonal anti-neurofilament 160/200 kD antibody (Zymed Lab., USA) was used, and as a secondary antibody, fluoresceinisothiocyanate (FITC) was used. At the time of staining amyloid beta, thioflavin-S was used.

RNA was extracted from the harvested brain tissue, cDNA was synthesized, and a real-time polymerase chain reaction (real-time PCR) was performed thereon, thereby confirming degree of expression of each of the proteins. If necessary, an amount of mRNA was quantified using a GAPDH gene.

Figure 4:
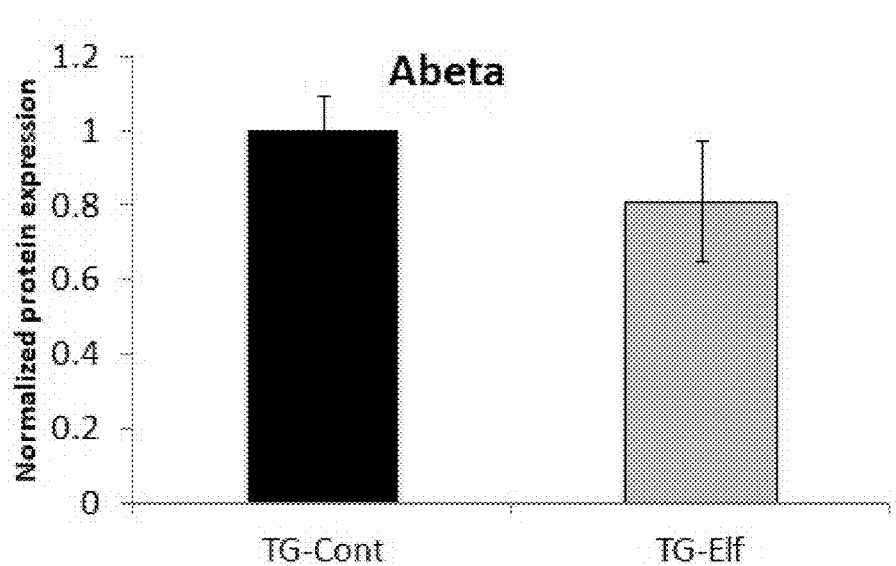
FIG. 4 illustrates changes in beta-amyloid (Aβ) expression by *Lactobacillus reuteri* ELF (accession number: KCTC 13154BP) in Alzheimer's disease-induced mice.
Figure 5:
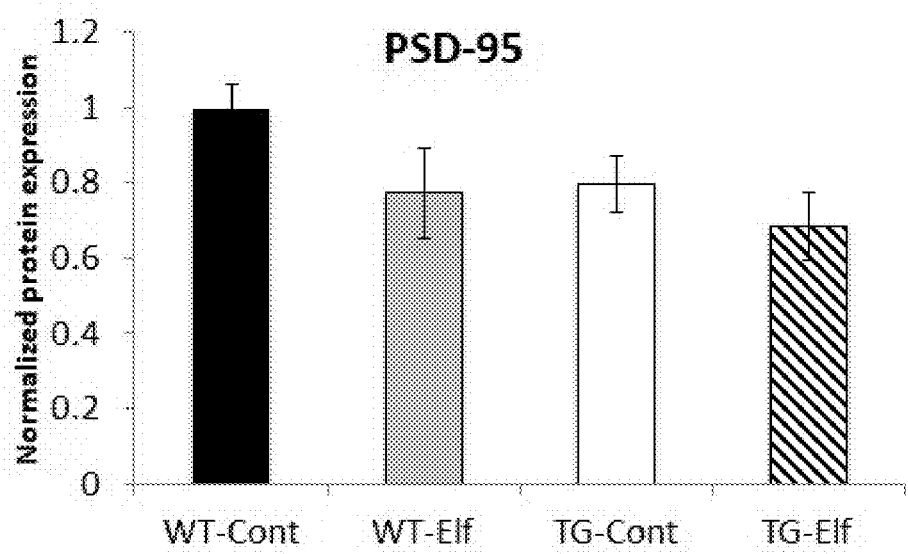
FIG. 5 illustrates changes in postsynaptic density protein-95 (PSD-95) expression by *Lactobacillus reuteri* ELF (accession number: KCTC 13154BP) in normal mice and Alzheimer's disease-induced mice.
Figure 6:
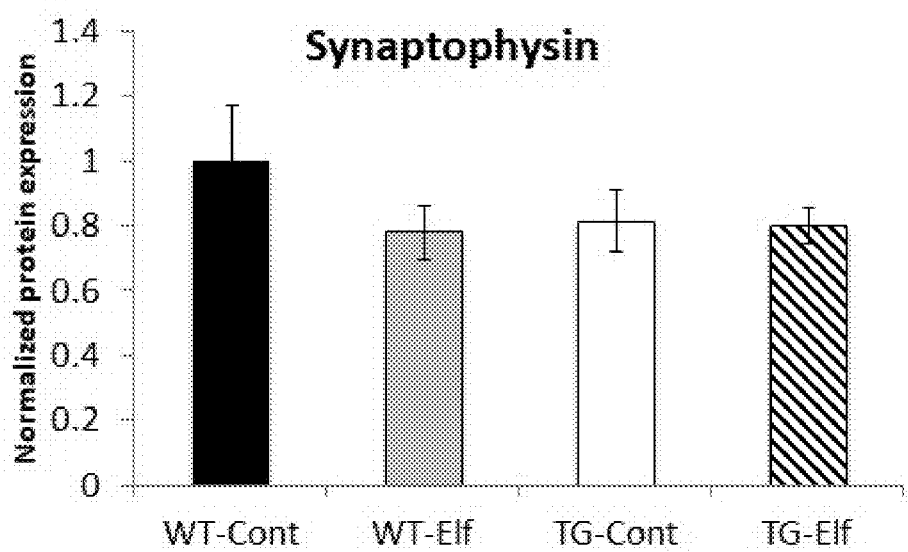
FIG. 6 illustrates changes in synaptophysin expression by *Lactobacillus reuteri* ELF (accession number: KCTC 13154BP) in normal mice and Alzheimer's disease-induced mice.

As an experimental result, in the mice with Alzheimer's disease, which were fed with the feed containing *Lactobacillus reuteri* ELF, beta amyloid expression was reduced by about 20% (FIG. 4). Further, postsynaptic density protein-95 (PSD-95) expression was also reduced by about 15% in the mice with Alzheimer's disease, which were fed with the feed containing *Lactobacillus reuteri* ELF, a significant effect was exhibited (FIG. 5). On the contrary, there was not much change in synaptopyhysin expression (FIG. 6).

Figure 7:
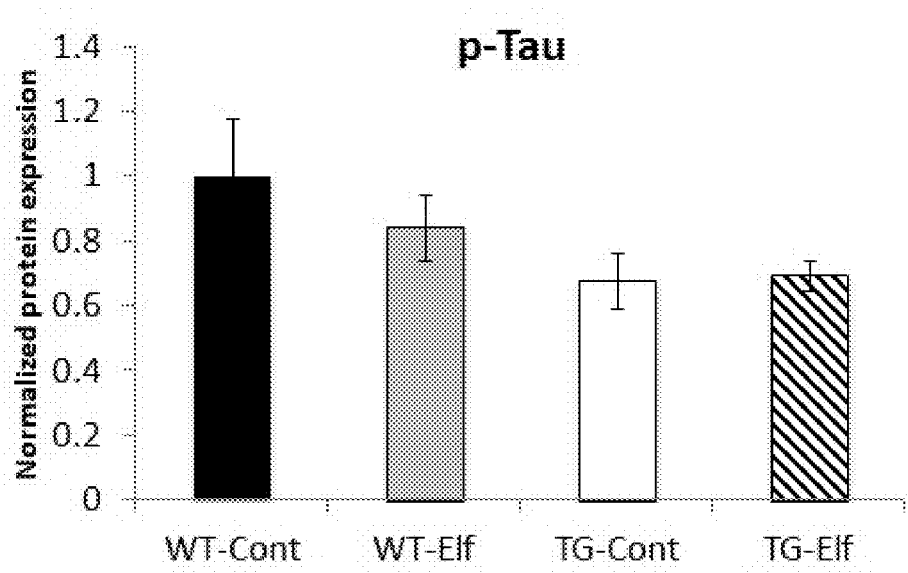
FIG. 7 illustrates changes in phosphorylated tau protein (p-Tau) expression by *Lactobacillus reuteri* ELF (accession number: KCTC 13154BP) in normal mice and Alzheimer's disease-induced mice.
Figure 8:
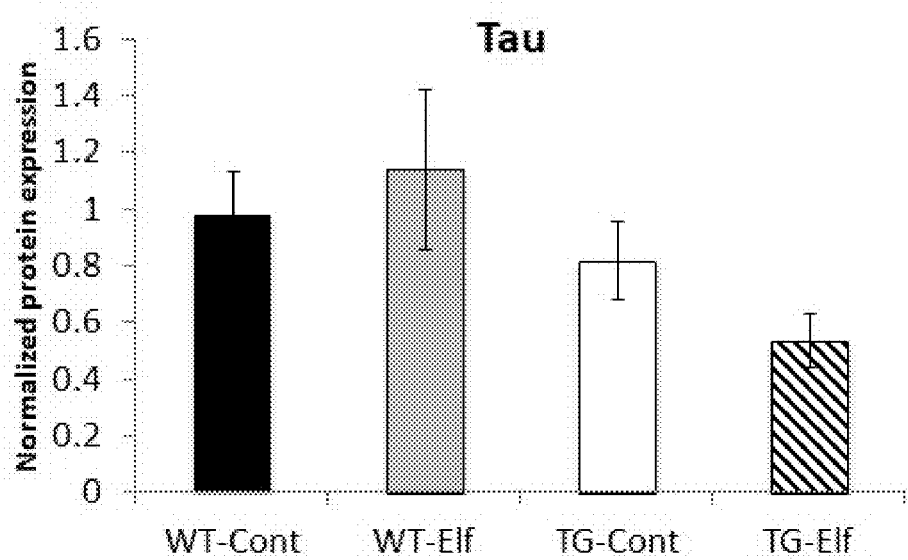
FIG. 8 illustrates changes in tau protein (Tau) expression by *Lactobacillus reuteri* ELF (accession number: KCTC 13154BP) in normal mice and Alzheimer's disease-induced mice.
Figure 9:
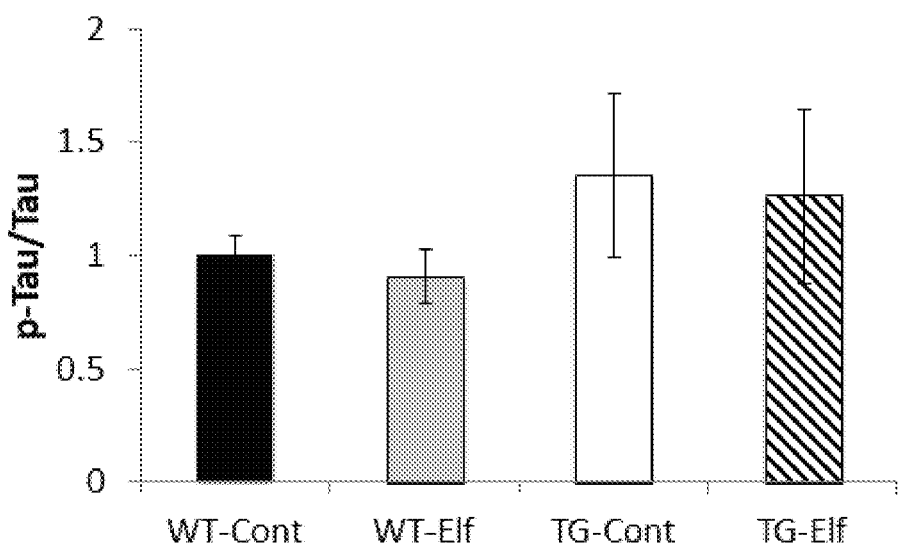
FIG. 9 illustrates changes in expression ratio between phosphorylated tau protein (p-Tau) and tau protein (Tau) by *Lactobacillus reuteri* ELF (accession number: KCTC 13154BP) in normal mice and Alzheimer's disease-induced mice.

There was not much change in phosphorylated tau protein (p-Tau) (FIG. 7). However, in the mice with Alzheimer's disease, which were fed with the feed containing *Lactobacillus reuteri* ELF, tau protein expression was reduced by about 25% (FIG. 8).

Figure 10:
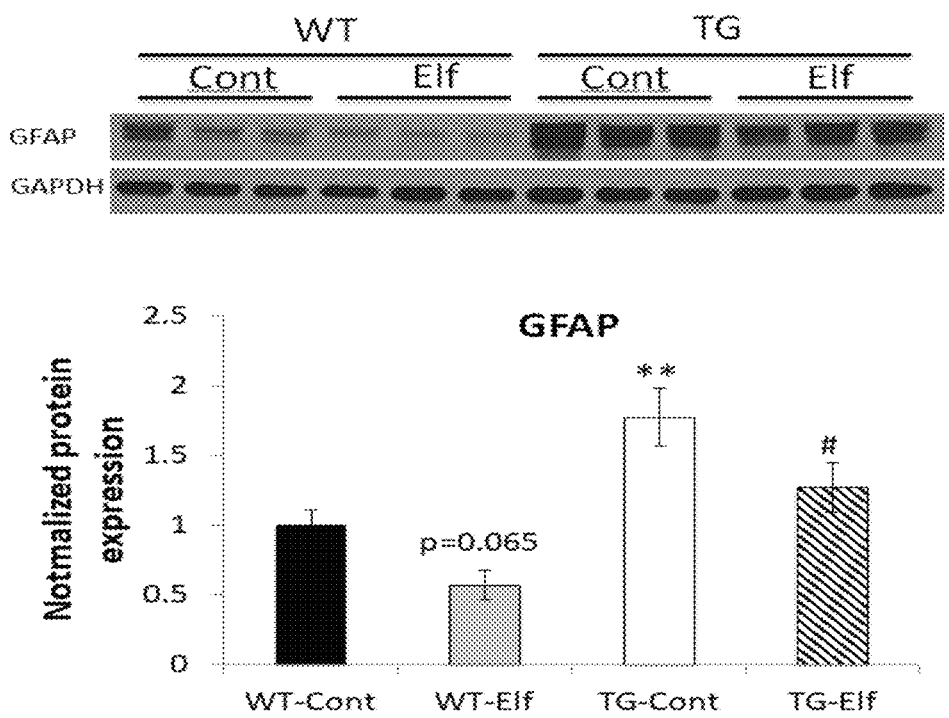
FIG. 10 illustrates changes in glial fibrillary acidic protein (GFAP) expression by *Lactobacillus reuteri* ELF (accession number: KCTC 13154BP) in normal mice and Alzheimer's disease-induced mice.
Figure 11:
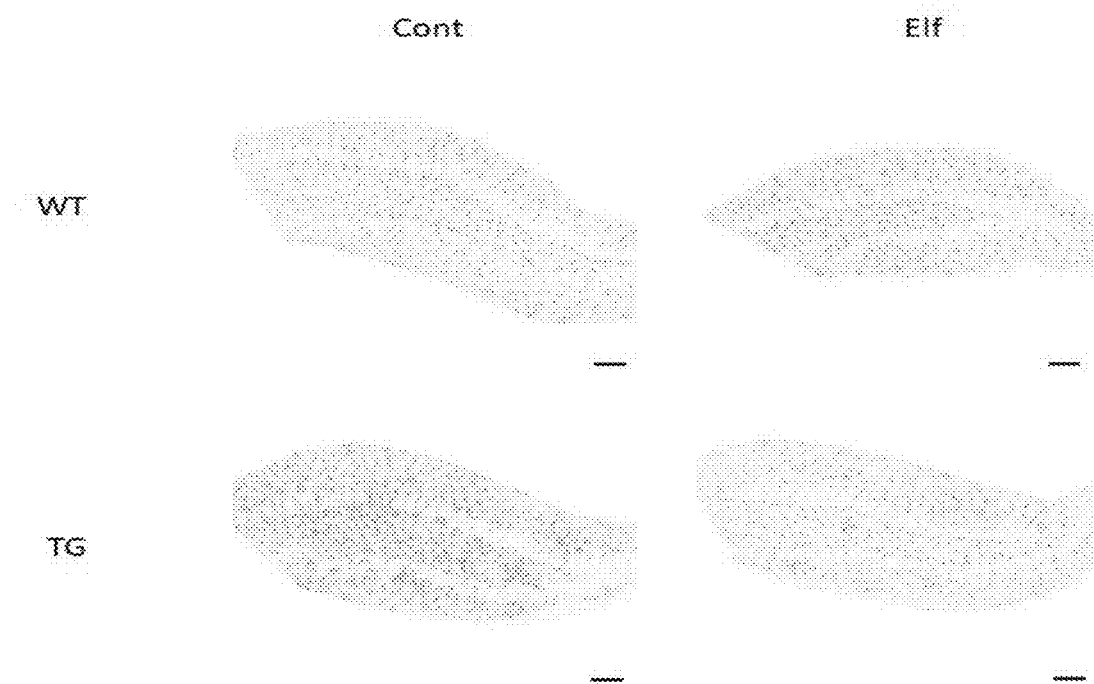
FIG. 11 illustrates staining states of glial fibrillary acidic protein (GFAP) in the dentate gyrus (DG) of the hippocampus of normal mice and Alzheimer's disease-induced mice fed with *Lactobacillus reuteri* ELF (accession number: KCTC 13154BP) (scale bar=100 μm).

Glial fibrillary acidic protein (GFAP) expression was significantly increased in the mice with Alzheimer's disease. However, in the mice with Alzheimer's disease, which were fed with the feed containing *Lactobacillus reuteri* ELF, GFAP expression was reduced by about 30% (FIGS. 10 and 11).

Figure 12:
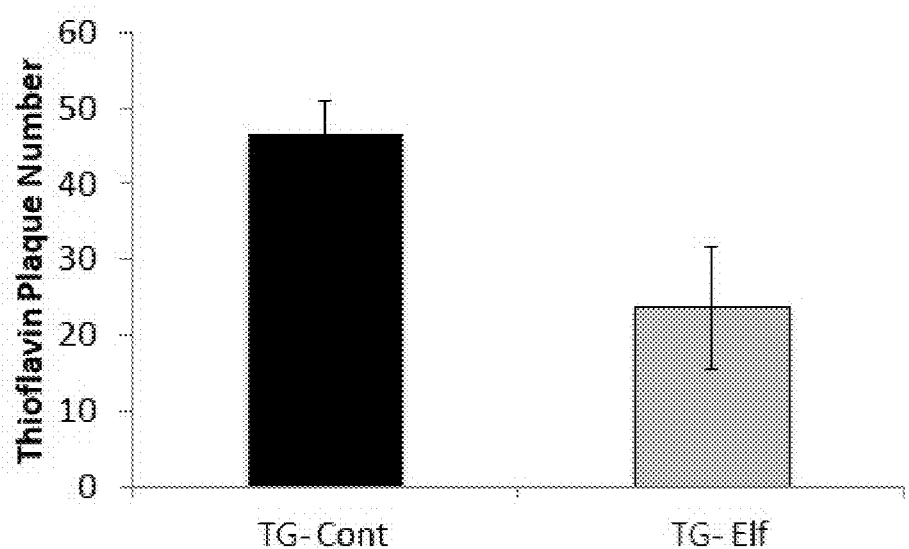
FIG. 12 illustrates a change in beta-amyloid (Aβ) plaque by *Lactobacillus reuteri* ELF (accession number: KCTC 13154BP) in Alzheimer's disease-induced mice.
Figure 13:
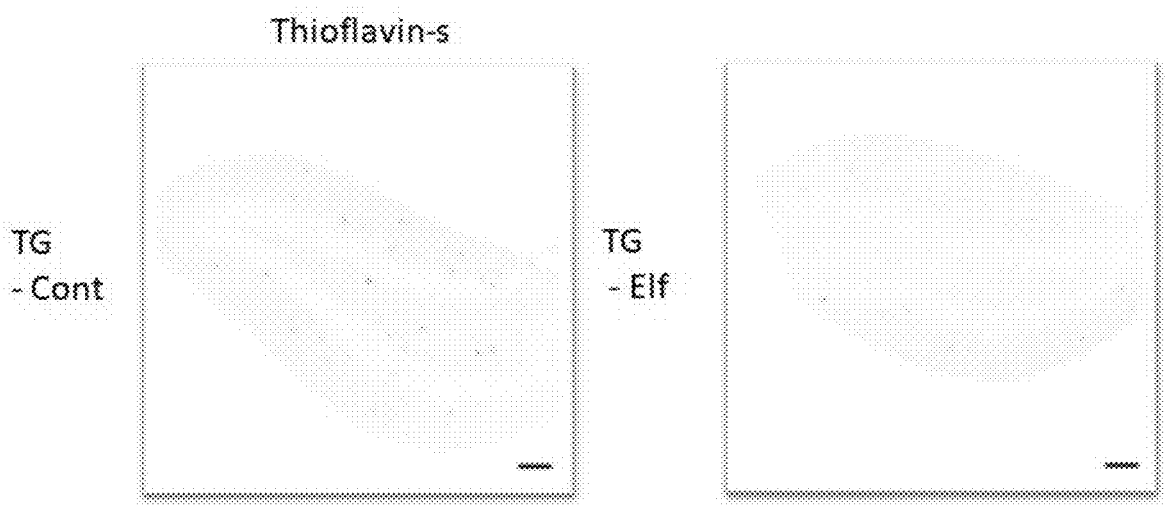
FIG. 13 illustrates staining states of beta-amyloid (Aβ) in the dentate gyrus (DG) of the hippocampus of normal mice and Alzheimer's disease-induced mice fed with *Lactobacillus reuteri* ELF (accession number: KCTC 13154BP) (scale bar=100 μm).

As a result obtained by measuring amyloid plaques using thioflavin-S, in the mice with Alzheimer's disease, which were fed with the feed containing *Lactobacillus reuteri* ELF, amyloid plaque formation was reduced by about 50% (FIGS. 12 and 13).

Example 7

Preparation of Composition Containing *Lactobacillus reuteri* ELF and 5-Aminolevulinic Acid 3000 ml of distilled water and 431 g of anhydrous sodium carbonate ($Na_2CO_3$) were put into and stirred in a 4 L incubator, and 130 g of cysteine hydrochloride salt was added thereto. After removing dissolved oxygen by stirring the mixture while injecting and bubbling nitrogen thereinto, 200 g of 5-aminolevulinic acid was added thereto and dissolved therein. A pH was adjusted to 8.6 to 9.5 using hydrochloric acid and sodium carbonate. As lactic acid bacteria, 400 g of *Lactobacillus reuteri* ELF isolated in Example 2 was added thereto, and stirred, thereby obtaining a uniform suspension. The culturing was performed by stirring the mixture at 30° C. for 24 hours. Thereafter, 1000 ml of 1M calcium lactate solution was added thereto and stirred for 1 hour, and then centrifugation (5000 rpm, 10 minutes) was performed thereon, thereby precipitating and obtaining a composition containing *Lactobacillus reuteri* ELF and 5-aminolevulinic acid. Metabolites by metabolism of the lactic acid bacteria in addition to *Lactobacillus reuteri* ELF and 5-aminolevulinic acid were also contained in the obtained composition. If necessary, the obtained precipitate was freeze-dried to completely remove water, and then the resultant was packaged and stored.

Example 8

Concentration Analysis of Metabolite by Metabolism of Lactic Acid Bacteria in Composition Containing *Lactobacillus reuteri* ELF and 5-Aminolevulinic Acid 20 µl of the culture solution in Example 7 was added to 2 ml of Ehrlich reagent. Since when porphobilinogen, and the like, containing pyrrole was formed as the metabolite of 5-aminolevulinic acid by metabolism of the lactic acid bacteria, strong absorption (red color) was shown at a wavelength of 550 nm, an absorbance value was measured. A concentration of the metabolite of 5-aminolevulinic acid was measured through the absorbance value which was in proportional to pyrrole ((Absorbance) $\lambda 550$=2.3, 0.45%).

Example 9

Analysis of Metabolites by Metabolism of Lactic Acid Bacteria in Composition Containing *Lactobacillus reuteri* ELF and 5-Aminolevulinic Acid 200 ml of anion exchange resin (Trilite, SAR20MB, Samyang Corp.) was prepared in a column, and 25% sodium acetate aqueous solution was allowed to sufficiently flow therein, thereby saturating anions with acetic acid. Here, this process was continued until a white precipitation was not formed at the time of dropping a silver nitrate aqueous solution to an eluate. The column was washed with distilled water, and a pH of the eluate was adjusted to be 7.5 or less.

1 g of the composition freeze-dried in FIG. 7 was dispersed in 10 ml of 1N acetic acid. After centrifugation (5,000 rpm, 5 minutes), a pH of a supernatant was adjusted to 7, and the supernatant was passed through the above-mentioned column. The resultant was washed with a sufficient amount of distilled water, eluted again with 1N acetic acid, and 1N acetic acid solution passed through and discharge from the column was freeze-dried. Then, the freeze-dried material was dissolved using $D_2O$ as a solvent, and metabolites were confirmed using $^1H$ nuclear magnetic resonance ($^1H$ NMR) spectroscopy. As a result of $^1H$ NMR, peaks were observed at 5.8 (s, 1H), 4.3 (s, 2H), 3.6 (s, 2H), 2.7 (t, 2H), 2.5 (t, 2H), and thus, it was confirmed that one of the metabolites was porphobilinogen. In a result of $^1H$ NMR before analysis using the column, significantly various metabolites including porphobilinogen were contained, such that a significantly complicated peak was observed.

Example 10

In order to confirm an immune enhancing effect, changes in IL-2, IL-4, IL-10, and IFN-γ caused by proliferation and activation of T lymphocytes were measured in the peripheral blood mononuclear cells (PBMC) and the spleen.

Balb/c based male mice (8 weeks old) were divided into a vehicle control group, a group in which 5-aminolevulinic acid (hereinafter, referred as 'ALA', 100 mg/kg) was orally administered for 14 days (2 weeks), a group in which *Lactobacillus reuteri* ELF (hereinafter, referred to as 'LAB', 100 mg/kg) was orally administered for 14 days (2 weeks), a group in which a mixture sample (50 mg/kg) of *Lactobacillus reuteri* ELF and 5-aminolevulinic acid (hereinafter, referred to as 'ALA+LAB') was orally administered for 14 days (2 weeks), and a group in which the mixture sample (100 mg/kg) of *Lactobacillus reuteri* ELF and 5-aminolevulinic acid was orally administered for 14 days (2 weeks).

Example 10-1

Fluorescence Flow Cytometry Analysis of Activated T Lymphocytes in PBMC and Spleen After 2 weeks of administration, in order to obtain PBMC in the mice, the blood was extracted using a syringe (3 ml) treated with heparin by a cardiac puncture method. The extracted blood was mixed and treated with 10 ml of ACK solution (a solution obtained by mixing 8.3 g of $NH_4Cl$ and 1 g of $KHCO_3$ with demineralized water to which 0.1 Mm EDTA was added) prepared in advance at room temperature for 5 minutes, thereby removing red blood cells. The spleen was harvested, and spleen cells were isolated with a 100 mesh filter, subjected to centrifugation at 1700 rpm for 5 minutes using D-PBS, washed, and then passed through a cell strainer (FALCON), thereby removing tissue or impurities that were not decomposed except for cells. The isolated PBMC and spleen cells were washed two times with PBS containing 1% fetal bovine serum (FBS) as a FACS buffer and then passed through the cell trainer, thereby removing impurities except for the cells. After the number of PBMC cells in each test tube was adjusted to be $5 \times 10^5$ cells, immunofluorescence staining was performed thereon at 4° C. In each test tube, anti-CD3e-PE, anti-CD25-FITC, anti-CD4-FITC, anti-CD69-FITC, anti-CD44-cy5.5-PE, anti-CTLA-4-FITC, anti-NK1.1-PE, and anti-CD49b-FITC were injected, and a reaction was carried out on ice for 30 minutes. Thereafter, the resultants were washed with PBS three times or more, and frequencies (%) of activated $CD4^+$ $CD25^+$, $CD44^+$ $CD69^+$, $CD49b^+$ $NK1.1^+$, and $CD25^+$ $CTLA-4^+$ cells were analyzed using a cell quest program of flow cytometry.

Figure 14:
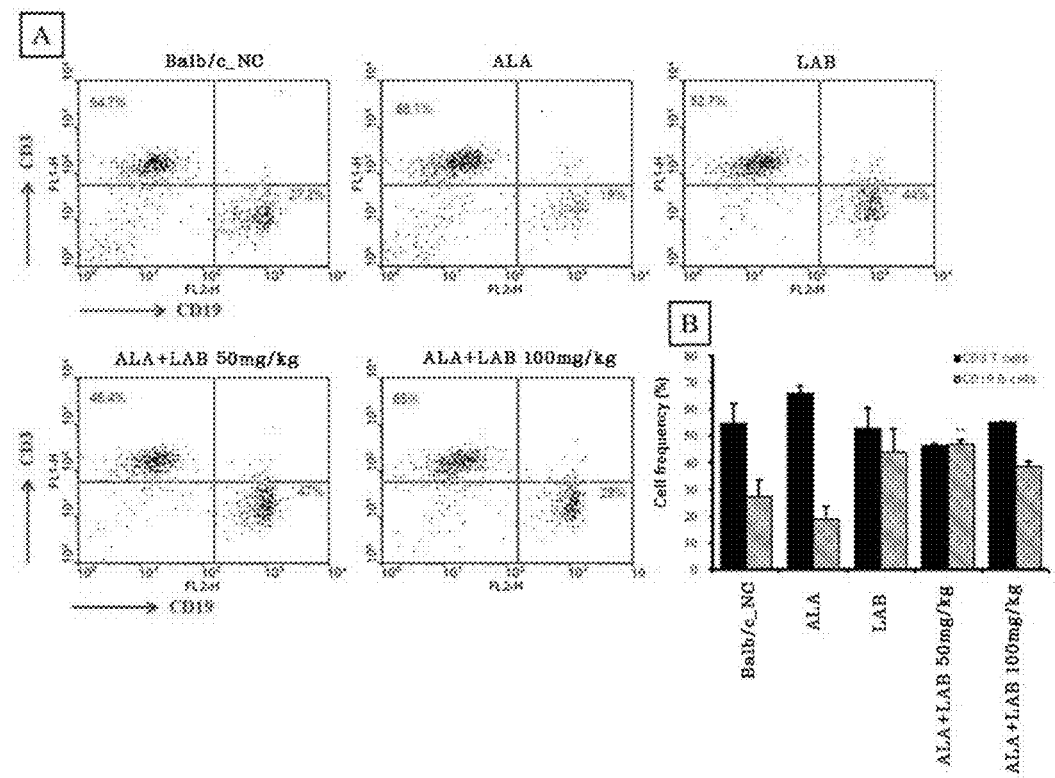
FIG. 14 illustrates changes in frequency of CD3 T cells according to example 10.
Figure 15:
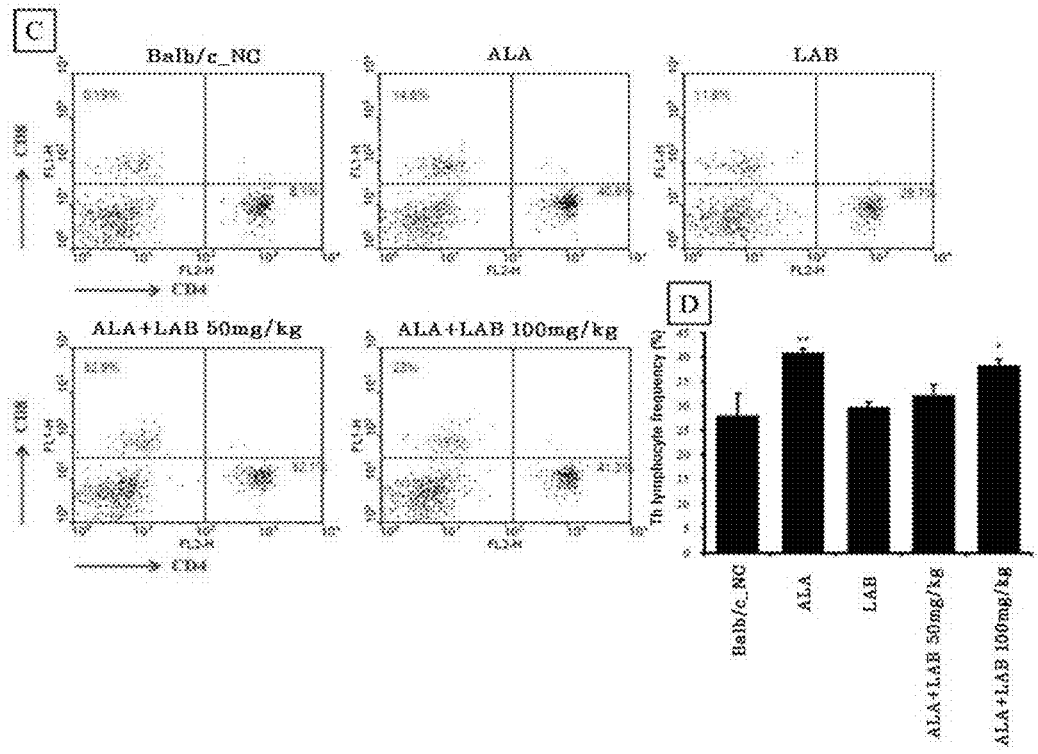
FIG. 15 illustrates changes in Th lymphocytes according to example 10.
Figure 16:
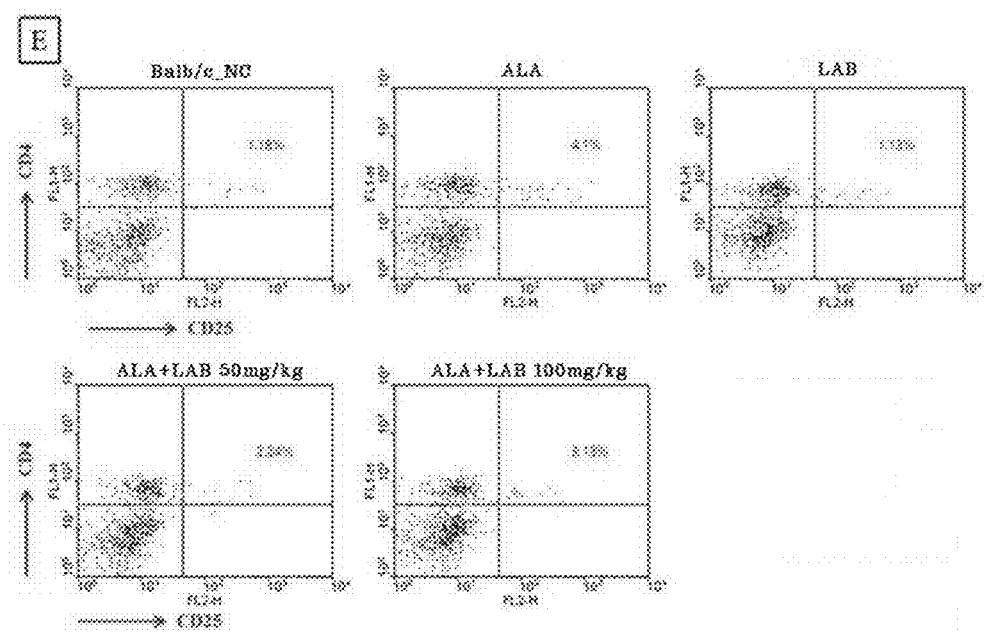
FIG. 16 illustrates changes in frequency of CD4+ CD25+ cells according to example 10.
Figure 17:
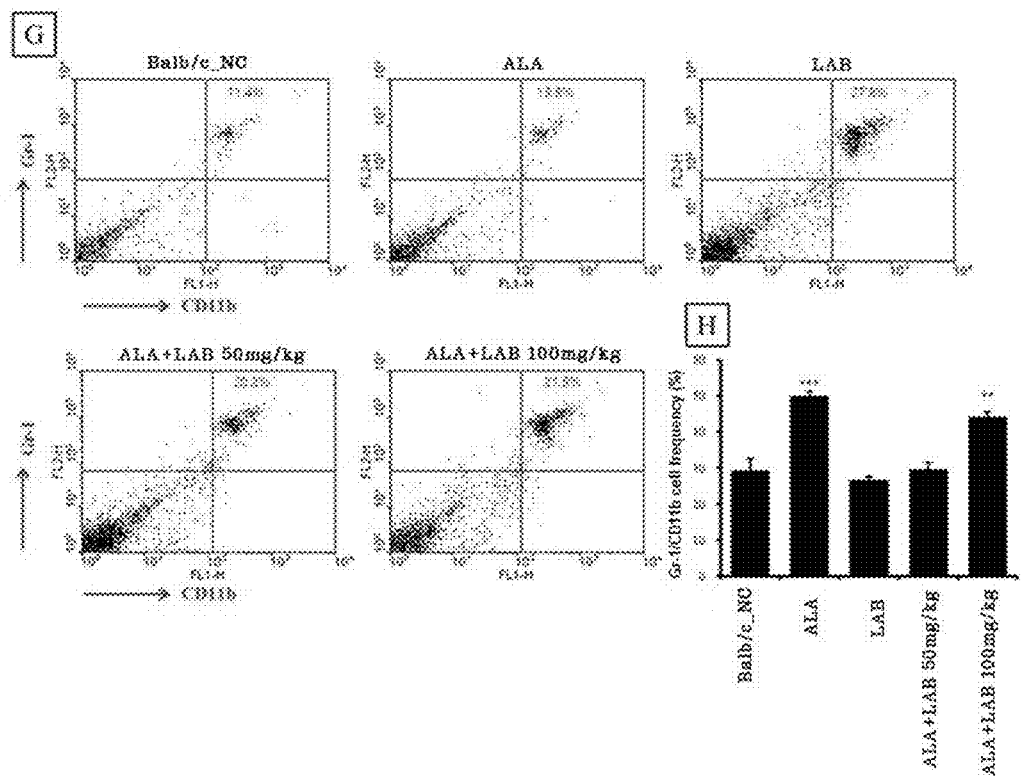
FIG. 17 illustrates changes in frequency of Gr-1/CD11b cells according to example 10.
Figure 18:
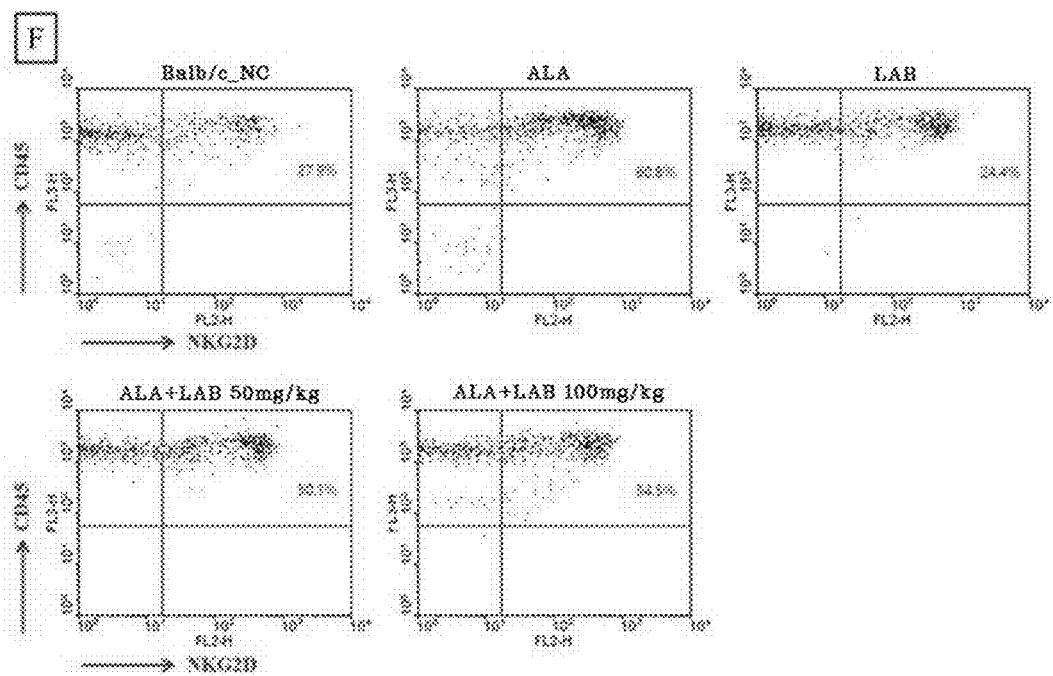
FIG. 18 illustrates changes in frequency of natural killer group 2 member D (NKG2D), which is a bioactive marker of NK cells according to example 10.

As a result of the analysis, the frequency of activated Th lymphocytes in PBMC after oral administration of the feed for 2 weeks in a negative control group (NC) was 27.9%, and a group in which *Lactobacillus reuteri* ELF was administered, the frequency was slightly increased as compared to the negative control group. Further, a group in which 5-aminolevulinic acid (100 mg/kg) was administered, the frequency of activated Th lymphocytes was increased by 46.2% or more as compared to the negative control group. In the groups in which 50 mg/kg and 100 mg/kg of the mixture sample of *Lactobacillus reuteri* ELF and 5-aminolevulinic acid were administered, respectively, the frequency of the activated Th lymphocytes was increased to 15% and 36.9% (C and D of FIG. 15). The frequency of CD3 T cells was increased in the group in which 100 mg/kg of 5-aminolevulinic acid was administered and the groups in which 50 mg/kg and 100 mg/kg of the mixture sample of *Lactobacillus reuteri* ELF and 5-aminolevulinic acid were administered, respectively, (A and B of FIG. 14) as compared to the control group, but there was no difference in the frequency of CD19 B cells between the groups. Further, the frequency of $CD4^+$ $CD25^+$ cells (FIG. 16) and Gr-1/CD11b cells (G and H of FIG. 17) were significantly increased in the groups in which 100 mg/kg of 5-aminolevulinic acid was administered and the group in which 100 mg/kg of the mixture sample of *Lactobacillus reuteri* ELF and 5-aminolevulinic acid was administered as compared to the control group. In addition, the frequency of NKG2D (FIG. 18) corresponding to a bioactive marker of NK cells was significantly increased in the group in which 5-aminolevulinic acid (100 mg/kg) was administered and the groups in which the mixture sample (50 mg/kg and 100 mg/kg) of *Lactobacillus reuteri* ELF and 5-aminolevulinic acid was administered as compared to the control group. That is, it may be confirmed that in the mice to which the mixture sample containing *Lactobacillus reuteri* ELF and 5-aminolevulinic acid was administered, the immune enhancing effect was significantly improved due to a synergistic effect of the metabolites formed through metabolism of 5-aminolevulinic acid by *Lactobacillus reuteri* ELF in addition to *Lactobacillus reuteri* ELF and 5-aminolevulinic acid.

Example 10-2

Measurement of IFN-γ, IL-2, IL-4, and IL-10 Corresponding to Active Substances of Activated T Cells in Cultured Spleen Cells After 2 weeks of administration, the spleen was harvested from the mice, and spleen cells were isolated with a 100 mesh filter. Before one day of measurement, anti-CD3 mAb (1 µg/ml) was coated on a 96-well plate and kept overnight in a refrigerator at 4° C., and the 96-well plate was washed with D-PBS two times. After removing red blood cells from the isolated spleen cells using an ACK solution, the spleen cells ($5 \times 10^5$ cells) were inoculated in each well coated with anti-CD3 mAb, and cultured in a 5% FBS-DMEM culture medium for 48 hours, followed by centrifugation at 2,000 rpm for 3 minutes, thereby obtaining 200 µl of culture supernatant. Levels of IFN-γ, IL-2, IL-4, and IL-10 in the culture supernatant were measured by enzyme-linked immuno-sorbent assay (ELISA). After the culture supernatant (50 µl) was dispensed in each well, kept at room temperature (25° C.) for 2 hours and washed with washing buffer two times, a biotin-IL conjugated antibody was added thereto and kept for 2 hours. Again, each well was washed with the washing buffer two times, treated with 100 µl of avidin-horseradish peroxidase (HRP) conjugated antibody, and kept at room temperature for 1 hours, followed by washing again. 100 µl of tetramethylbenzidine (TMP) substrate solution was dispensed in each well and kept in the dark for 30 minutes, and then each well was treated with 100 µl of stop solution. Thereafter, absorbance was measured at 450 nm in an ELISA reader.

Figure 19:
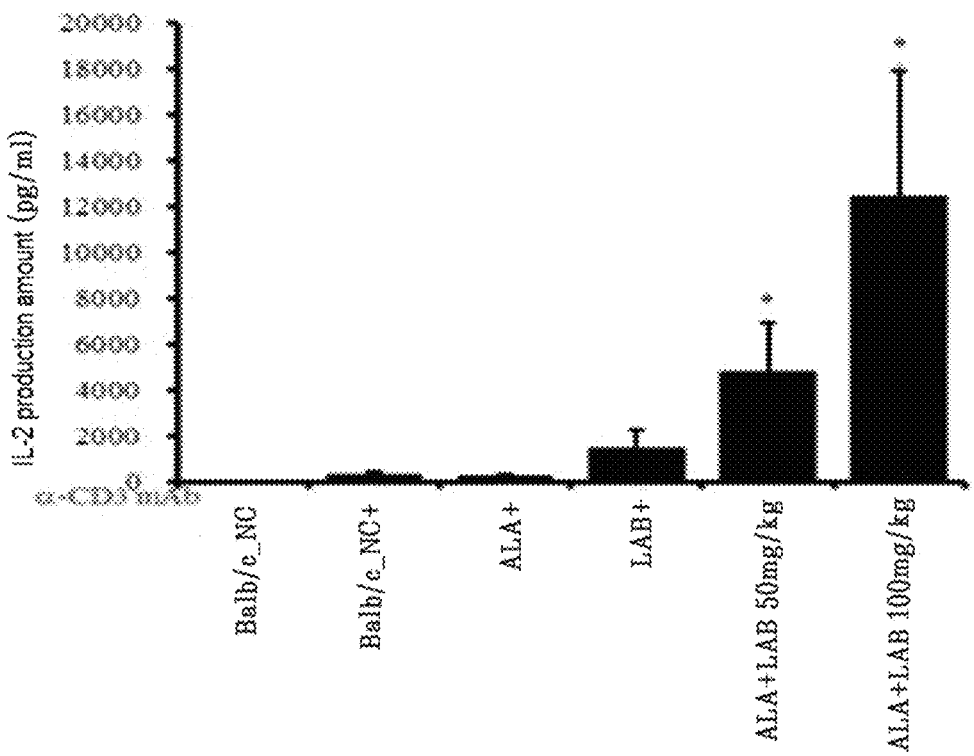
FIG. 19 illustrates changes in interleukin (IL)-2 production amount in splenocytes according to example 10.
Figure 20:
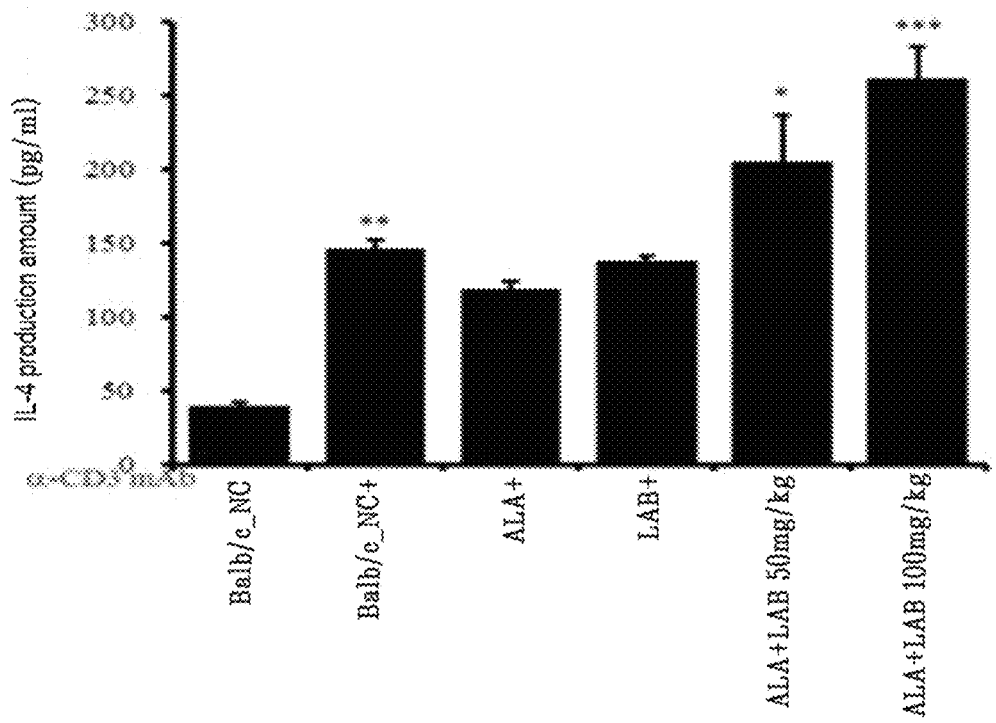
FIG. 20 illustrates changes in IL-4 production amount in splenocytes according to example 10.
Figure 21:
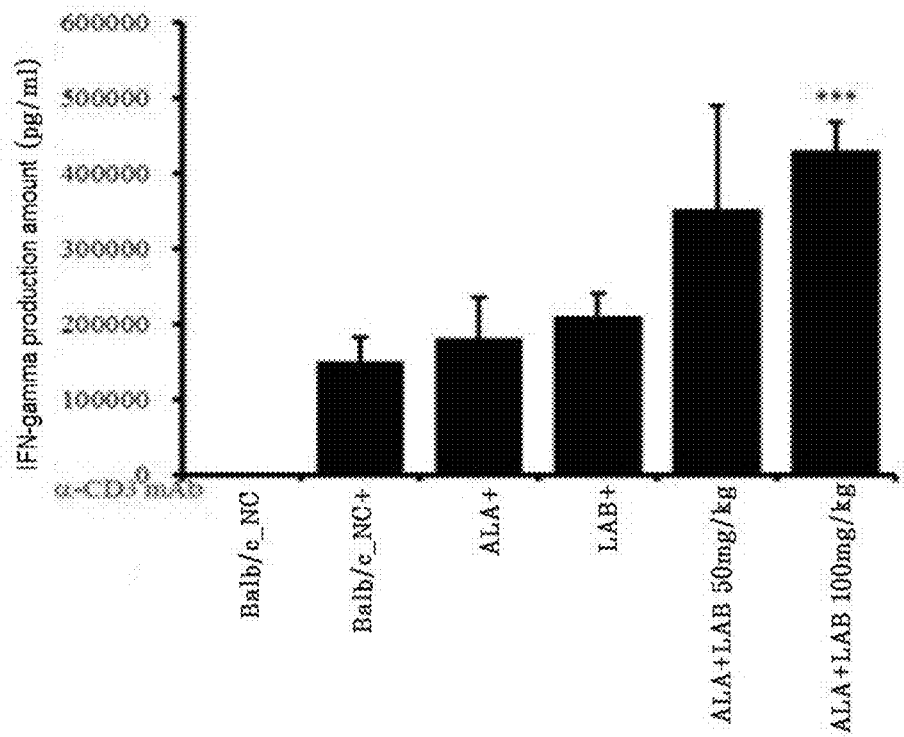
FIG. 21 illustrates changes in IFN-γ production amount in splenocytes according to example 10.

As a result of measurement, there was no difference in absorbance between the group in which *Lactobacillus reuteri* ELF was administered and the control group (NC), in the group in which 5-aminolevulinic acid (100 mg/kg) was administered, absorbance was increased two times or more, and in the groups in which the mixture sample (50 mg/kg and 100 mg/kg) of *Lactobacillus reuteri* ELF and 5-aminolevulinic acid was administered, absorbance was increased two times, and 2.57 times or more, respectively. Further, in the group in which *Lactobacillus reuteri* ELF was administered and the group in which 5-aminolevulinic acid (100 mg/kg) was administered, the IL-2 production amount (FIG. 19), the IL-4 production amount (FIG. 20), and the IFN-γ production amount (FIG. 21) were slightly increased as compared to control group (NC), and in the groups in which the mixture sample of *Lactobacillus reuteri* ELF and 5-aminolevulinic acid was administered, the IL-2 production amount, the IL-4 production amount, and the IFN-γ production amount were statistically significantly increased by about 2.1 times or more in dependence on the administration concentration as compared to the control group. That is, it may be confirmed that in the mice to which the mixture sample of *Lactobacillus reuteri* ELF and 5-aminolevulinic acid was administered, the immune enhancing effect was significantly improved due to the synergistic effect of the metabolites formed through metabolism of 5-aminolevulinic acid by *Lactobacillus reuteri* ELF in addition to *Lactobacillus reuteri* ELF and 5-aminolevulinic acid.

Example 11

In order to confirm an immune enhancing effect, a degree of increase in nitrogen oxide (NO) in macrophage was measured.

Example 11-1. Measurement of Nitrogen Oxide (NO) Formation in Macrophage

Balb/c based mice were divided into a vehicle control group, a group in which 5-aminolevulinic acid (100 mg/kg) was orally administered for 14 days (2 weeks), a group in which *Lactobacillus reuteri* ELF (100 mg/kg) was orally administered for 14 days (2 weeks), a group in which a mixture sample (50 mg/kg) of *Lactobacillus reuteri* ELF and 5-aminolevulinic acid was orally administered for 14 days (2 weeks), and a group in which the mixture sample (100 mg/kg) of *Lactobacillus reuteri* ELF and 5-aminolevulinic acid was orally administered for 14 days (2 weeks). Three days before termination of administration, after 1.5 ml of 10% proteose peptone (Difco) aqueous solution was administered into the abdominal cavity of the mice, the mice were sacrificed, and the abdomen was disinfected with alcohol. The skin of the abdomen was cut using scissors, and the peritoneum was exposed. Then, 4.5 ml of cooled Hanks' balanced salt solution (HBSS) was injected into the abdominal cavity using a syringe and abdominal massage was performed thereon for 30 seconds, followed by recovering a peritoneal washing fluid using a syringe. Recovered cells were cooled, washed with the same HBSS solution two times, suspended in a cooled RPMI1640 medium. Then, a concentration of the suspension was adjusted so that a viable cell count was $2 \times 10^6$ cells/ml at the time of calculating a viable cell count by trypan blue staining, and then the suspension (200 μl/well) was dispensed in a 96-well culture plate. After the suspension was cultured in a CO2 incubator for 1 to 2 hours to attach the macrophages to the wells, floating cells were removed by washing the 96-well culture plate with HBSS solution three times at 37° C., and 100 μl of RPMI 1640 medium was added thereto. After culturing the resultant in the CO2 incubator for 72 hours, a culture supernatant was recovered and cryopreserved. 100 μl of culture supernatant was collected and mixed with 2 ml of distilled water and 200 μl of Griese reagent I in which 0.5 g of sulfanilamide was dissolved in a mixed solution of 25 ml of strong hydrochloric acid and 25 ml of distilled water. In addition, after 200 μl of Griese reagent II in which 0.06 g of N-1-naphthylene amidehydrochloride was dissolved in 50 ml of distilled water was rapidly added thereto, and stirred, absorbance was measured at 540 nm.

Figure 22:
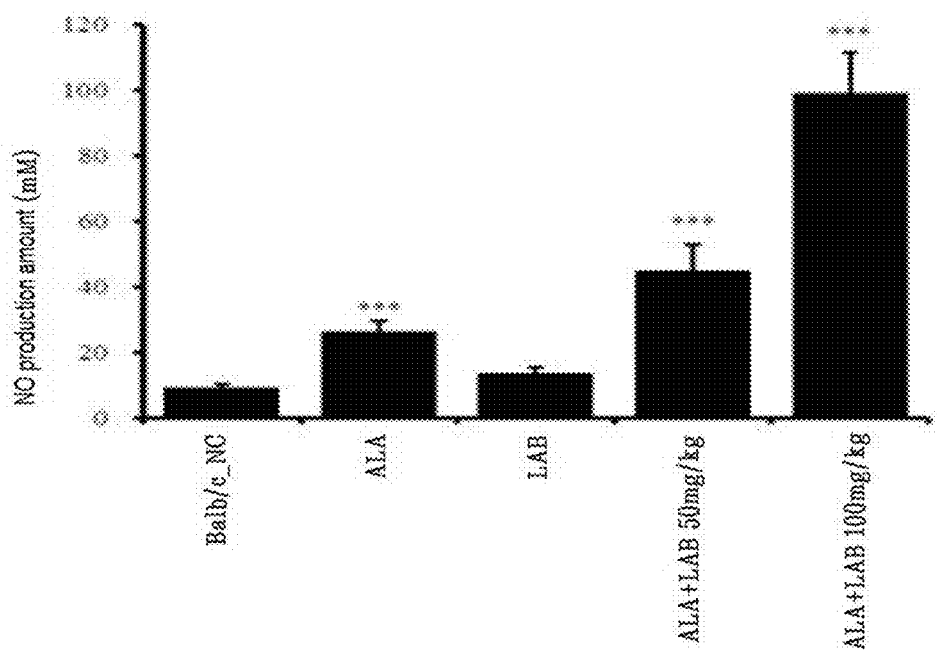
FIG. 22 illustrates changes in production amount of nitric oxide in macrophages according to example 11.

As a result of measurement, in the group in which 5-aminolevulinc acid (100 mg/kg) was administered and the groups in which the mixture sample (50 mg/kg and 100 mg/kg) of *Lactobacillus reuteri* ELF and 5-aminolevulinic acid was administered, respectively, the nitrogen oxide (NO) production amount was statistically significantly increased as compared to the control group (NC). Further, in the group in which the mixture sample of *Lactobacillus reuteri* ELF and 5-aminolevulinic acid was administered, the nitrogen oxide (NO) production amount was significantly increased by two times or more as compared to the group in which 5-aminolevulinc acid was administered alone (FIG. 22). That is, it may be confirmed that in the mice to which the mixture sample containing *Lactobacillus reuteri* ELF and 5-aminolevulinic acid was administered, the immune enhancing effect was significantly improved due to the synergistic effect of the metabolites formed through metabolism of 5-aminolevulinic acid by *Lactobacillus reuteri* ELF in addition to *Lactobacillus reuteri* ELF and 5-aminolevulinic acid.

Example 11-2. Measurement of Influence on Proliferation of Peritoneal Cell Population Balb/c based mice were divided into a vehicle control group, a group in which 5-aminolevulinic acid (100 mg/kg) was orally administered for 14 days (2 weeks), a group in which *Lactobacillus reuteri* ELF (100 mg/kg) was orally administered for 14 days (2 weeks), a group in which a mixture sample (50 mg/kg) of *Lactobacillus reuteri* ELF and 5-aminolevulinic acid was orally administered for 14 days (2 weeks), and a group in which the mixture sample (100 mg/kg) of *Lactobacillus reuteri* ELF and 5-aminolevulinic acid was orally administered for 14 days (2 weeks). Two days before termination of administration, 0.5 ml of 2% normal saline suspension of starch was injected into the abdominal cavity of the mice to thereby be immunized. The mice were sacrificed, and the abdomen was disinfected with alcohol. Then, the skin of the abdomen was cut using scissors and the peritoneum was exposed. Thereafter, 5 ml of cooled Hanks' balanced salt solution (HBSS) was injected into the abdominal cavity using a syringe and abdominal massage was performed thereon for 30 seconds, followed by recovering peritoneal washing fluid (about 3 ml) using a syringe. After recovered cells were cooled, washed with the same HBSS solution two times, the number of peritoneal cells existing therein was directly measured using a hemocytometer under a microscope. The peritoneal washing fluid of which a total peritoneal cell count was terminated was subjected to centrifugation at 4° C. and 400 g for 10 minutes to obtain cell precipitates, and then the cell precipitates were suspended with PBS. After the number of peritoneal cells in each test tube was adjusted to $5 \times 10^5$, immunofluorescence staining was performed at 4° C. After anti-CD11b-FITC, anti-CD3-cy5.5-PE, anti-CD4-FITC, anti-CD8-FITC, and anti-CD14-PE were put into each test tube and a reaction was carried out on ice for 30 minutes. Thereafter, the resultants were washed with PBS three times or more, and frequencies (%) of activated $CD11b^+$ $CD14^+$, $CD3^+$ $CD4^+$, and $CD3^+$ $CD8^+$ cells were analyzed using the Cell Quest program of a flow cytometry, and a total cell count was applied thereto, thereby calculating the absolute number of peritoneal cell population.

Figure 23:
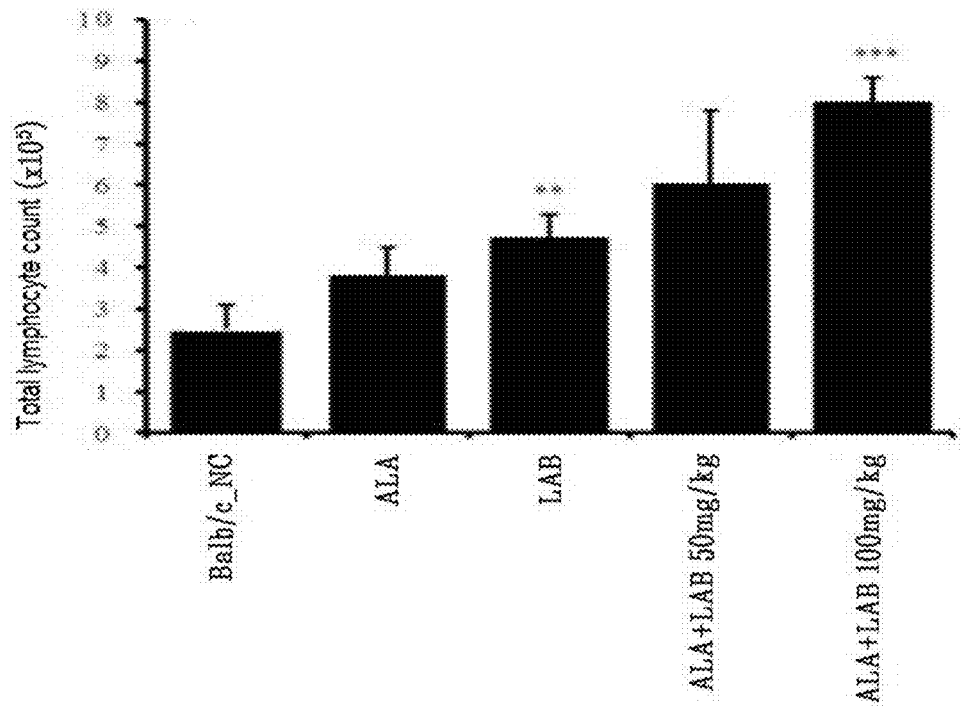
FIG. 23 illustrates changes in total lymphocyte count according to example 11.

As a result of calculation, in all of the groups in which *Lactobacillus reuteri* ELF, 5-aminolevulinic acid, and the mixture sample of *Lactobacillus reuteri* ELF and 5-aminolevulinic acid were administered, respectively, the number of lymphocytes was increased as compared to the control group. However, the number of lymphocytes was further increased in the group in which *Lactobacillus reuteri* ELF and 5-aminolevulinic acid were administered. Particularly, it may be confirmed that in the group in which the mixture sample (100 mg/kg) of *Lactobacillus reuteri* ELF and 5-aminolevulinic acid was administered, the number of lymphocytes was significantly increased (FIG. 23). That is, it may be confirmed that in the mice to which the mixture sample containing *Lactobacillus reuteri* ELF and 5-aminolevulinic acid was administered, the immune enhancing effect was significantly improved due to the synergistic effect of the metabolites formed through metabolism of 5-aminolevulinic acid by *Lactobacillus reuteri* ELF in addition to *Lactobacillus reuteri* ELF and 5-aminolevulinic acid.

Example 12

Measurement of COX Activity in Liver Mitochondria

Figure 24:
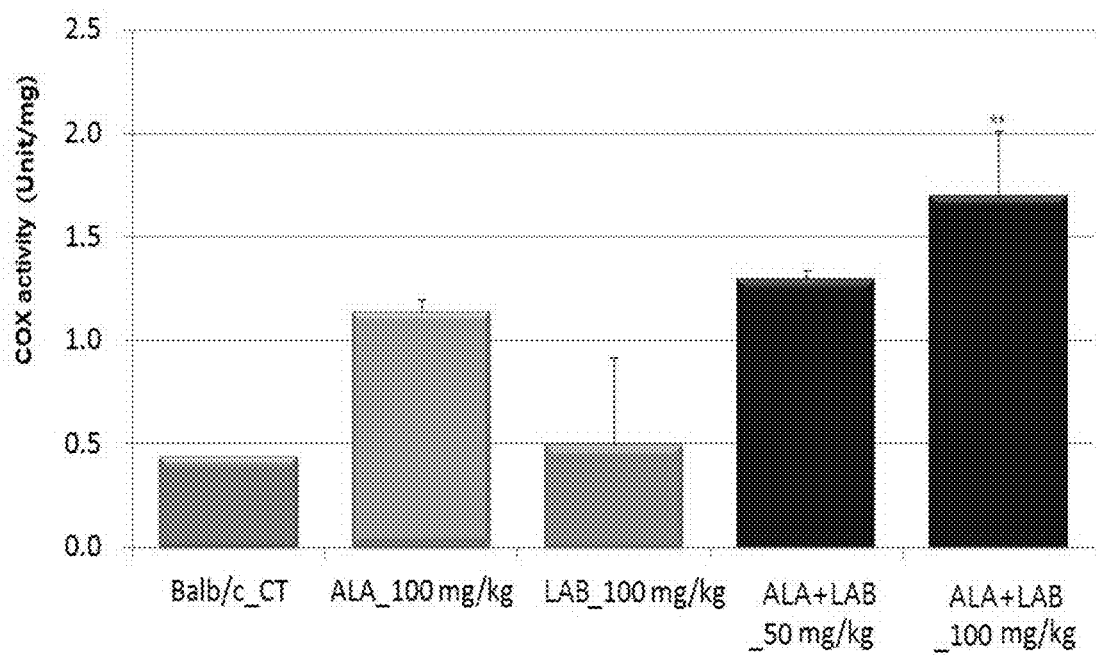
FIG. 24 illustrates activities of cytochrome oxidase (COX) in the liver according to example 12.

Balb/c based mice were divided into a vehicle control group, a group in which 5-aminolevulinic acid (100 mg/kg) was orally administered for 14 days (2 weeks), a group in which *Lactobacillus reuteri* ELF (100 mg/kg) was orally administered for 14 days (2 weeks), and a group in which the mixture sample (100 mg/kg) of *Lactobacillus reuteri* ELF and 5-aminolevulinic acid was orally administered for 14 days (2 weeks). In order to measure cytochrome c oxidase (COX) activity in the liver mitochondria of the mouse after administration, proteins were extracted from the liver cells of the mouse and measured using a COX activity assay kit (TA100, Toyo B Net). As a result of measurement, there was no difference in the COX activity between the control group and the group in which *Lactobacillus reuteri* ELF (LAB) was administered, and in the group in which 5-aminolevulinic acid (ALA) was administered, the COX activity was increased by two times or more, but there was no statistical significance. It was confirmed that in the group in which ALA and LAB were administered ($p<0.01$), the COX activity was statistically significantly increased by four times or more (FIG. 24). That is, it may be confirmed that in the mice to which the mixture sample containing *Lactobacillus reuteri* ELF and 5-aminolevulinic acid was administered, an effect to increasing the COX activity was significantly improved due to the synergistic effect of the metabolites formed through metabolism of 5-aminolevulinic acid by *Lactobacillus reuteri* ELF in addition to *Lactobacillus reuteri* ELF and 5-aminolevulinic acid.

Example 13

Measurement of COX Activity in Brain Mitochondria

Figure 25:
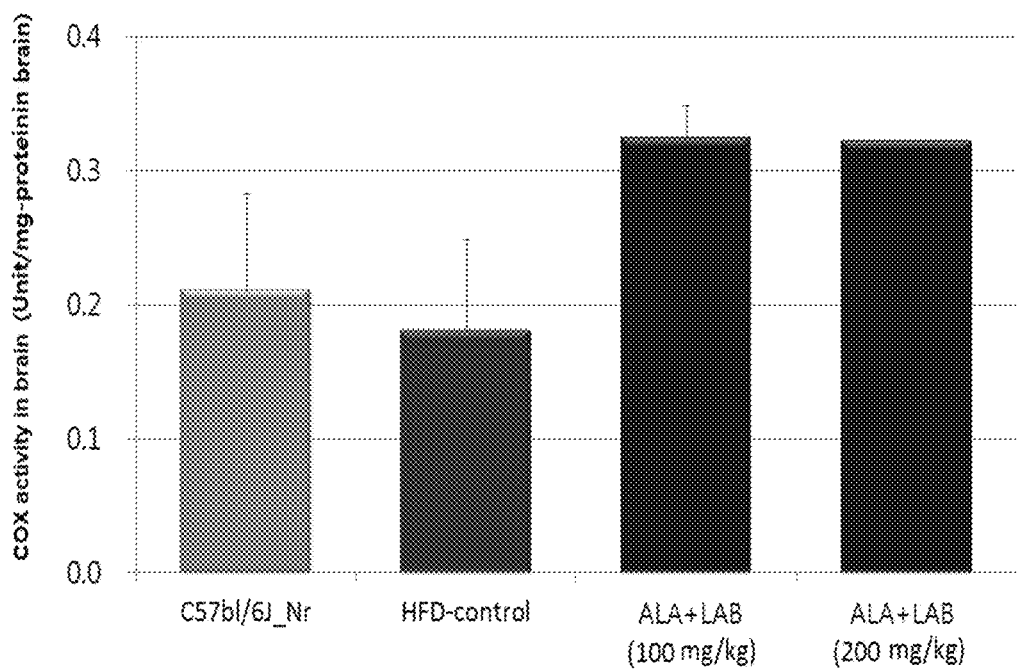
FIG. 25 illustrates activities of cytochrome oxidase (COX) in the brain according to example 13.

C57BL/6J mice (vehicle control group) as a normal control group and an obesity control group (high-fat diet (HFD) control) were prepared. In the obesity control group (high-fat diet (HFD) control), after adapting 8-week old male C57BL/6J mice (Daehan Biolink Corp.) for 2 weeks under a specific pathogen-free (SPF) environment at a constant temperature (25±2° C.) and a constant humidity (50±5%) with a light period of 12 hours (light on 07:00 to 19:00) while freely supplying basic feed (AIN-76A diet) and water, high-fat diet (# D12492 60 kcal fat, Research Diets Inc, USA) was administered from 10 weeks of age (at this time, the mice had a body weight of about 24 g or more), thereby preparing a diet-induced obesity (DIO) mouse model. 100 mg/kg and 200 mg/kg of a mixture sample of *Lactobacillus reuteri* ELF and 5-aminolevulinic acid (ALA+LAB) were administered to the obesity control group, respectively, for 14 days (2 weeks) together with high-fat diet from 10 weeks of age. After oral administration was terminated, in order to measure cytochrome oxidase (COX) activity in the brain mitochondria of the mouse, the brain of the mouse was harvested, and the COX activity of the brain was measured according to a user's manual of a COX activity assay kit (TA100, Toyo B Net). As a result of measurement, the COX activity was decreased in the obesity control group as compared to the normal control group, and the group in which ALA and LAB were administered (ALA+LAB) ($p<0.01$), the COX activity was statistically significantly increased by 1.5 times or more as compared to the normal control group (FIG. 25).

That is, it may be confirmed that in the mice to which the mixture sample containing *Lactobacillus reuteri* ELF and 5-aminolevulinic acid was administered, the COX activity was significantly improved due to the synergistic effect of the metabolites formed through metabolism of 5-aminolevulinic acid by lactic acid bacteria in addition to *Lactobacillus reuteri* ELF and 5-aminolevulinic acid. Further, it may be confirmed that the mixture sample is not affected by the blood-brain barrier in the brain but may directly affect an increase in COX activity in the brain mitochondria. It may be appreciated from the result described above that the mixture of *Lactobacillus reuteri* ELF and 5-aminolevulinic acid is effective to treat a degenerative brain disease caused by a decrease in COX activity in the brain mitochondria.

Example 14

Confirmation of Change in Body Weight of Mouse Using Obesity Control Group

Figure 26:
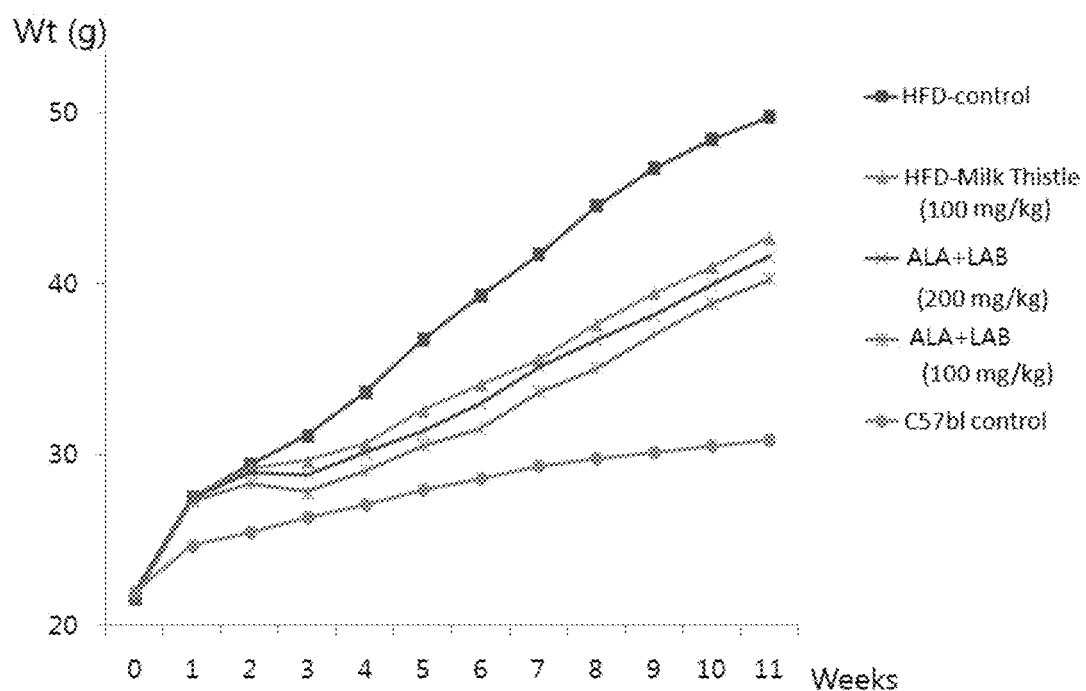
FIG. 26 illustrates changes in body weight according to example 14.

An obesity control group (HFD) was prepared in the same manner as in Example 13, and 100 mg/kg and 200 mg/kg of mixed sample (ALA+LAB) of *Lactobacillus reuteri* ELF and 5-aminolevulinic acid, and 100 mg/kg of milk thistle (MTS) were administered, respectively, together with high-fat diet from 10 weeks to 19 weeks of age. A change in body weight was measured as follows: ① A change in body weight (wt) was measured and recorded at 9 o'clock every Wednesday, ② Total body wt gain: Final body wt−initial body wt, ③ daily average body wt gain=Total body wt gain/days. Finally, when the mice were 19 weeks old, in the groups in which MTS (100 mg/kg) ($p<0.001$), ALA+LAB (200 mg/kg) ($p<0.01$), and ALA+LAB (100 mg/kg) ($p<0.01$) were administered, respectively, the body weight was significantly decreased as compared to the obesity control group (FIG. 26).

Example 15

Oral Tolerance Test Using Obesity Control Group

Figure 27:
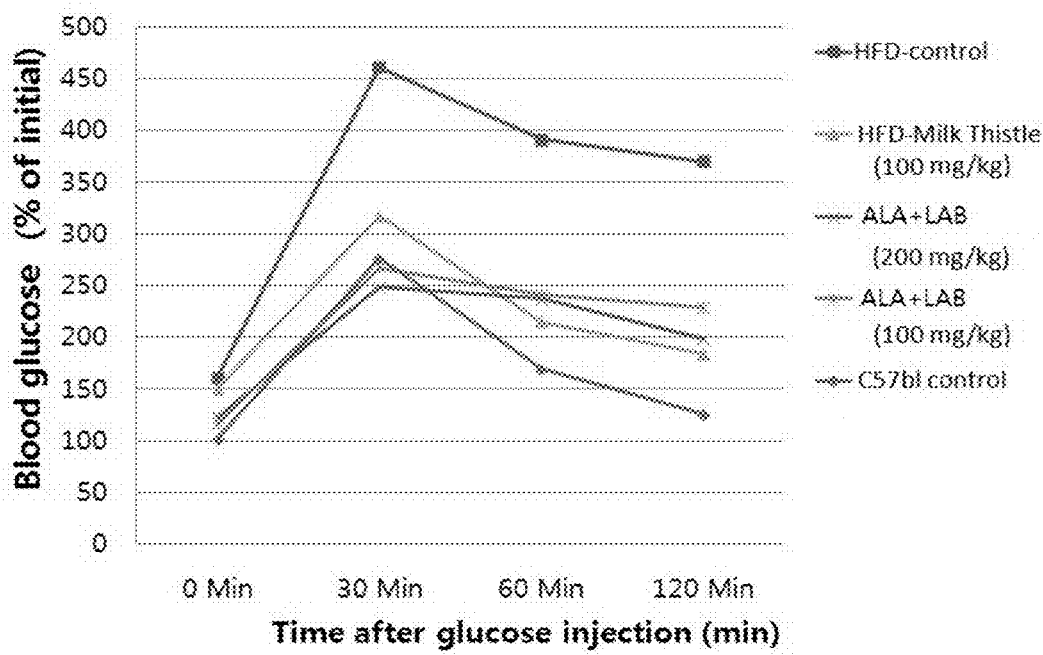
FIG. 27 illustrates results of an oral glucose tolerance test according to example 15.

In an oral glucose tolerance test, when glucose is orally ingested, glucose is absorbed in the intestinal tract beyond the ability to metabolize in the liver or tissue, such that a blood glucose level reaches a maximum value within 30 to 60 minutes. In addition, glucose is used in the tissue, glucose release in the liver is suppressed, and the blood glucose level is lowered by mechanisms to enhance insulin secretion and inhibit growth hormone secretion, and the like. An obesity control group was prepared in the same manner as in Example 13, and then, each test sample was administered together with glucose. As a result of oral administration (FIG. 27), in the oral glucose tolerance test in the obesity control group, a blood glucose level was increased three times or more at 30 minutes after administration of glucose and then slightly decreased even after 120 minutes. However, in the groups in which MTS (100 mg/kg) ($p<0.05$) and ALA+LAB (200 mg/kg) ($p<0.05$) were administered, respectively, the blood glucose level was statistically significantly decreased at 30, 60, and 120 minutes. In the groups in which ALA+LAB (100 mg/kg) was administered, the blood glucose level was decreased at 30, 60, and 120 minutes as compared to the obesity control group.

Example 16

Figure 28:
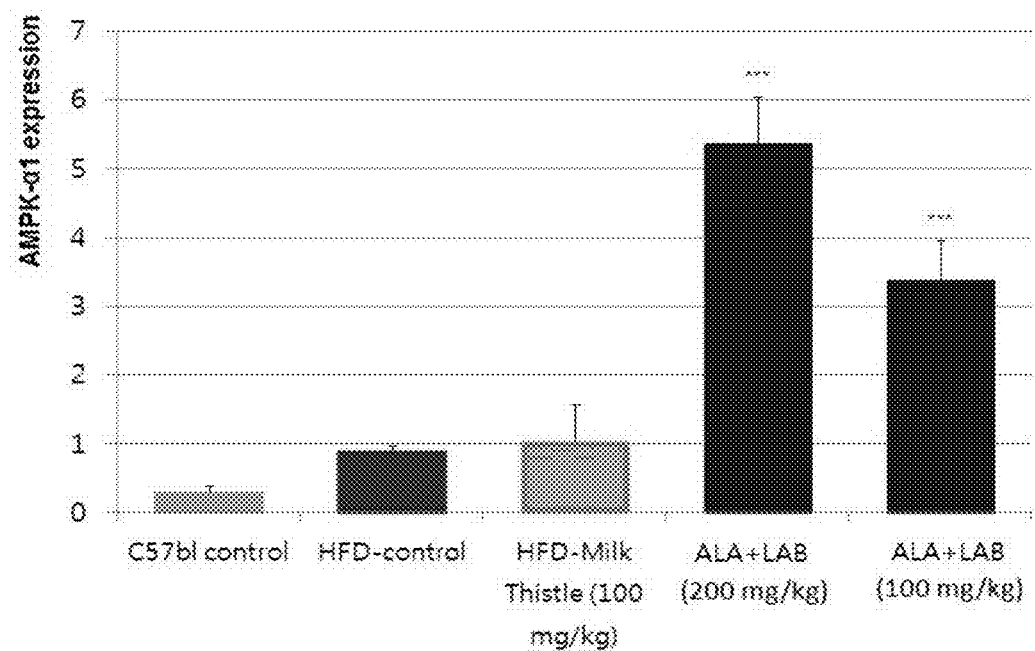
FIG. 28 illustrates AMPK-α1 gene expression pattern according to example 16.

Analysis of Gene Expression Pattern of AMPK-α1 Corresponding to Target Protein of Obesity and Diabetes A detailed analysis method was as follows. After measuring body weights according to Example 14, in a normal control group, a fat control group, and groups in which test samples was administered, respectively, RNA was extracted from liver tissue of each of the mice using RNAsolB (Tel-Test) solution. Thereafter, cDNA was prepared from RNA and real-time PCR analysis was performed thereon using an one-step SYBR Green PCR kit (AB science). After 500 μl of RNAzolB was added to the tissue, and the tissue was crushed by a homogenizer, 50 μl of chloroform ($CHCl_3$) was added thereto and mixed therewith for 15 seconds. After the mixture was kept on ice for 15 minutes and subjected to centrifugation at 13,000 rpm, about 200 μl of supernatant was recovered. The recovered supernatant was mixed with 200 μl (the same amount) of 2-propanol, slowly shaken, and kept on ice for 15 minutes. The mixture was subjected to centrifugation again at 13,000 rpm, the mixture was washed with 80% ethanol (EtOH), and dried in a vacuum pump for 3 minutes, thereby extracting RNA. The extracted RNA was dissolved in 20 μl of distilled water treated with diethyl pyrocarbonate (DEPC), inactivated at 75° C. on a heating block, and then used to synthesize first strand cDNA. At the time of performing a reverse transcription reaction, 3 μg of prepared total RNA was reacted with DNase I (10 U/μl) 2 U/tube on a heating block at 37° C. for 30 minutes, and denatured at 75° C. for 10 minutes. Then 2.5 μl of 10 mM dNTPs mix, 1 μl of random sequence hexanucleotides (25 pmole/25 μl), 1 μl of RNase inhibitor (20 U/μl) as an RNA inhibitor, 1 μl of 100 mM DTT, 4.5 μl of 5×RT buffer (250 mM Tris-HCl, pH 8.3, 375 mM KCl, 15 mM $MgCl_2$) were added thereto, 1 μl of M-MLV RT (200 U/μl) was added thereto again, and distilled water treated with DEPC was added thereto so that a final volume of a reaction mixture solution was 20 μl. 20 μl of the reaction mixture solution was well mixed and subjected to centrifugal sedimentation at 2,000 rpm for 5 seconds, and then a reaction was performed on a heating block at 37° C. for 45 minutes, thereby synthesizing the first-strand cDNA. Then, the resultant was kept at 95° C. for 5 minutes to inactivate Moloney Murine leukemia virus reverse transcriptase (M-MLV RT), and then, the synthesized cDNA was used in a polymerase chain reaction (PCR). A real-time quantitative PCR was performed using Applied Biosystems 7500 Real-Time PCR system (Applied Biosystems, USA). A primer sequence was as follow: 5'-AAGCCGACCCAATGACATCA-3' (SEQ ID NO: 1) was used as a forward primer, and 5'-CTTCCTTCG-TACACGCAAAT-3' (SEQ ID NO: 2) was used as a reverse primer. As a result of analyzing expression of AMPK-α1 mRNA expressed in the liver depending on the administration sample in the obesity mouse model, when a relative quantity (RQ) value of AMPK-α1 mRNA expression in the obesity control group was considered as 1, relative quantity values in experimental groups were analyzed. Expression of AMPK-α1 mRNA expressed in the liver in the obesity control group was similar to that in the normal control group (C57b1). There was not much difference in AMPK-α1 mRNA expression between the group in which MTS was administered and the obesity control group. However, in the groups in which ALA+LAB (200 mg/kg) ($p<0.001$) and ALA+LAB (100 mg/kg) ($p<0.001$) were administered, respectively, corresponding to experimental groups, AMPK-α1 mRNA expression was statistically significantly increased by 3 to 5 times or more (FIG. 28).

Example 17

Analysis of Gene Expression Pattern of Thermogenic Protein, UCP-2

Figure 29:
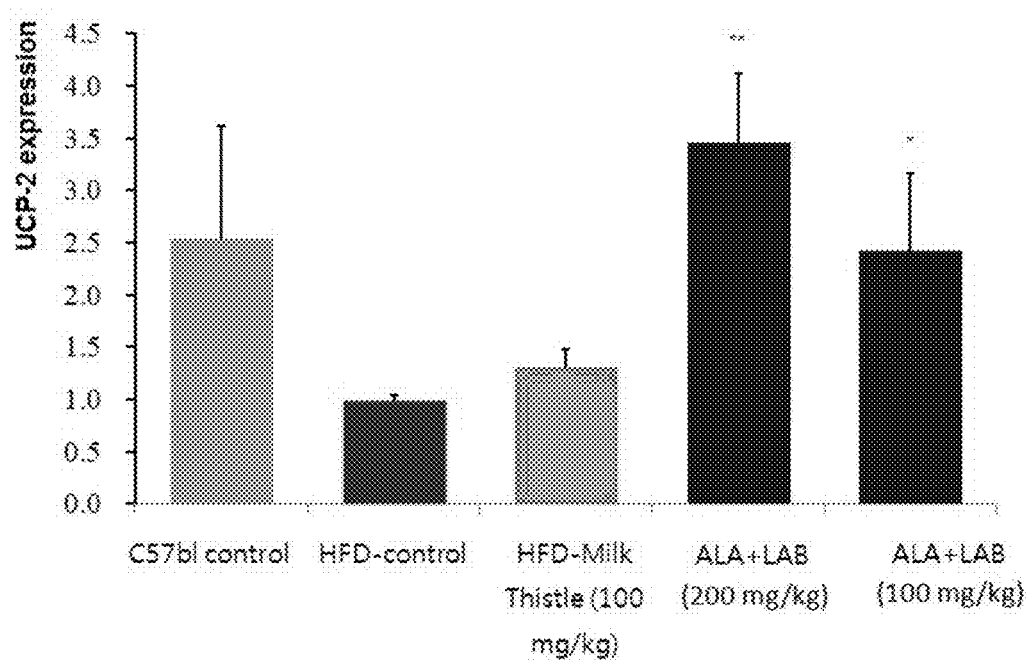
FIG. 29 illustrates UCP-2 gene expression pattern according to example 17.

After measuring body weights according to Example 14, in a normal control group, a fat control group, and groups in which test samples was administered, respectively, peripheral tissue of the liver of each of the mice was treated as in Example 10, and PCR was performed. 5'-TTCAAAT-GAGATTGTGGGAAAAT-3' (SEQ ID NO: 3) (sense) and 5'-ACCGATACAGTACAGTACAGTA-3' (SEQ ID NO: 4) (antisense) were used as probes. At the time of analysis, when a RQ value of UCP-2 mRNA expression in the obesity control group was considered as 1, relative quantity values in experimental groups were analyzed (FIG. 29). In the obesity control group, UCP-2 mRNA expression was significantly decreased as compared to the normal control group. In the experimental groups in which ALA+LAB (200 mg/kg) ($p<0.01$) and ALA+LAB (100 mg/kg) ($p<0.05$), etc., were administered, respectively, UCP-2 mRNA expression was statistically significantly increased as compared to the control group. However, in the experimental group in which MTS (100 mg/kg) was administered, UCP-2 mRNA expression was slightly increased as compared to the obesity control group, but this result was not statistically significant.

Example 18

Analysis of Gene Expression Pattern of Adiponectin

Figure 30:
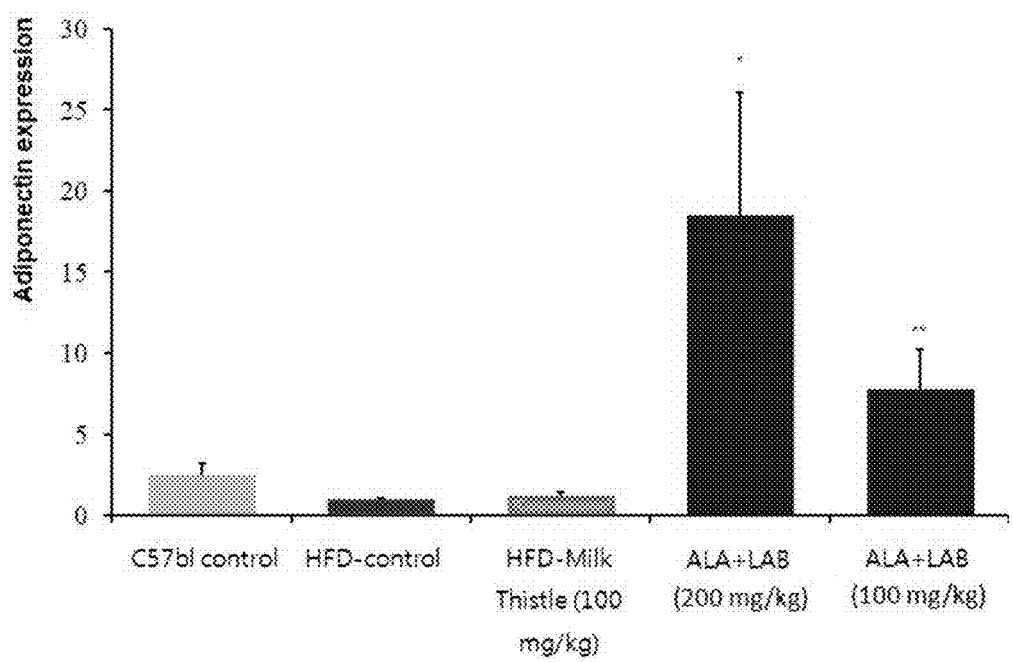
FIG. 30 illustrates adiponectin gene expression pattern according to example 18.

A gene expression pattern of adiponectin specifically expressed in adipocytes, increasing insulin sensitivity in the liver tissue, and increasing oxidation of fatty acids to reduce a body weight was analyzed. After measuring body weights according to Example 14, in a normal control group, a fat control group, and groups in which test samples was administered, respectively, peripheral tissue of the liver of each of the mice was treated as in Example 16, and PCR was performed. 5'-TTCAAATGAGATTGTGGGAAAAT-3' (SEQ ID NO: 3) (sense) and 5'-ACCGATACAGTACAG-TACAGTA-3' (SEQ ID NO: 4) (antisense) were used as probes. At the time of analysis, when a RQ value of adiponectin mRNA expression in the obesity control group (DIO-NC) was considered as 1, relative quantity values in experimental groups were analyzed. Expression of adiponectin mRNA expressed in the liver in the obesity control group was similar to that in the normal control group. There was not much difference in adiponectin mRNA expression between the group in which MTS was administered, which is a positive control group, and the obesity control group. However, in the groups in which ALA+LAB (200 mg/kg) (p<0.05) and ALA+LAB (100 mg/kg) (p<0.01) were administered, respectively, adiponectin mRNA expression was statistically significantly increased by 2 to 4 times or more (FIG. 30).

The invention claimed is:

1. A method of reducing tau protein expression and β-amyloid plaque formation comprising administering to a subject in need thereof a composition comprising a pure culture of *Lactobacillus reuteri* ELF, deposited under Accession Number KCTC 13154BP.

2. The method of claim 1, wherein the composition further comprises a pharmaceutically-acceptable carrier.

3. A method of increasing cytochrome c oxidase (COX) activity in brain mitochondria, comprising administering to a subject in need thereof a composition comprising a pure culture of *Lactobacillus reuteri* ELF, deposited under Accession Number KCTC 13154BP and 5-aminolevulinic acid.

4. The method of claim 3, wherein the composition further comprises a pharmaceutically-acceptable carrier.

* * * * *